United States Patent
Stack et al.

(10) Patent No.: US 11,307,274 B2
(45) Date of Patent: *Apr. 19, 2022

(54) METHOD AND SYSTEMS FOR A RADIO FREQUENCY COIL ASSEMBLY

(71) Applicant: General Electric Company, Schenectady, NY (US)

(72) Inventors: Ceara Delmore Stack, Ravenna, OH (US); Victor Taracila, Beachwood, OH (US); Fraser John Laing Robb, Aurora, OH (US)

(73) Assignee: General Electric Company, Schenectady, NY (US)

(*) Notice: Subject to any disclaimer, the term of this patent is extended or adjusted under 35 U.S.C. 154(b) by 371 days.

This patent is subject to a terminal disclaimer.

(21) Appl. No.: 16/001,793

(22) Filed: Jun. 6, 2018

(65) Prior Publication Data

US 2019/0377040 A1 Dec. 12, 2019

(51) Int. Cl.
*A61B 5/055* (2006.01)
*G01R 33/34* (2006.01)

(52) U.S. Cl.
CPC ........ *G01R 33/34084* (2013.01); *A61B 5/055* (2013.01); *G01R 33/34053* (2013.01)

(58) Field of Classification Search
CPC ........ G01R 33/34084; G01R 33/34053; G01R 33/3415; G01R 33/34092; G01R 33/34046; G01R 33/3642; G01R 33/36; G01R 33/385; G01R 33/34023; G01R 33/34007; G01R 33/3621; G01R 33/3628; G01R 33/34069; A61B 5/055
See application file for complete search history.

(56) References Cited

U.S. PATENT DOCUMENTS

| | | | |
|---|---|---|---|
| 6,980,000 B2* | 12/2005 | Wong | G01R 33/34053 324/318 |
| 7,663,367 B2 | 2/2010 | Wiggins | |
| 9,002,431 B2 | 4/2015 | Jones | |
| 10,274,555 B2* | 4/2019 | Findeklee | G01R 33/3635 |
| 10,859,648 B2 | 12/2020 | Robb | |
| 2005/0104591 A1* | 5/2005 | Qu | G01R 33/3415 324/318 |
| 2008/0174314 A1* | 7/2008 | Holwell | G01R 33/3415 324/318 |
| 2008/0204021 A1 | 8/2008 | Leussler et al. | |
| 2013/0093425 A1* | 4/2013 | Chu | G01R 33/365 324/318 |

(Continued)

OTHER PUBLICATIONS

Corea et al, "Screen-printed flexible MRI receive coils," Nature Communications vol. 7, Article No. 10839 (2016), 7 pages.

*Primary Examiner* — Catherine B Kuhlman
*Assistant Examiner* — Nicholas A Robinson

(57) ABSTRACT

Various methods and systems are provided for radio frequency (RF) coils for magnetic resonance imaging (MRI). In one embodiment, a radio frequency coil assembly for a magnetic resonance imaging system includes: a flexible spine; and at least two RF coil sections each coupled to the flexible spine and movable relative to each other, each RF coil section comprising at least one flexible RF coil, each RF coil including a loop portion comprising a coupling electronics portion and at least two parallel, distributed capacitance wire conductors encapsulated and separated by a dielectric material.

26 Claims, 13 Drawing Sheets

(56) References Cited

U.S. PATENT DOCUMENTS

| | | | |
|---|---|---|---|
| 2013/0137969 A1* | 5/2013 | Jones | A61B 5/055 600/421 |
| 2014/0091791 A1* | 4/2014 | Bulumulla | G01R 33/3642 324/309 |
| 2014/0103931 A1* | 4/2014 | Soutome | A61B 5/055 324/322 |
| 2014/0197832 A1* | 7/2014 | Driesel | H01Q 7/04 324/307 |
| 2014/0200437 A1* | 7/2014 | Yager | A61B 5/004 600/420 |
| 2014/0210466 A1 | 7/2014 | Arias et al. | |
| 2015/0017378 A1 | 1/2015 | Stone | |
| 2015/0168515 A1 | 6/2015 | Ishihara | |
| 2016/0356867 A1* | 12/2016 | Fujita | G01R 33/3642 |
| 2018/0335491 A1* | 11/2018 | Yang | G01R 33/341 |
| 2019/0154773 A1 | 5/2019 | Stack | |
| 2019/0154775 A1 | 5/2019 | Stack | |
| 2019/0277926 A1 | 9/2019 | Stormont | |
| 2019/0293738 A1* | 9/2019 | Popescu | G01R 33/3664 |
| 2019/0310327 A1 | 10/2019 | Stormont | |
| 2019/0369176 A1 | 12/2019 | Dalveren | |
| 2020/0081080 A1 | 3/2020 | Zemskov | |

\* cited by examiner

METHOD AND SYSTEMS FOR A RADIO FREQUENCY COIL ASSEMBLY

FIELD

Embodiments of the subject matter disclosed herein relate to medical diagnostic imaging, and in more particular, to systems for magnetic resonance imaging.

BACKGROUND

Magnetic resonance imaging (MRI) is a medical imaging modality that can produce images of an interior of a patient without x-ray radiation or other types of ionizing radiation. An MRI system is a medical imaging device utilizing a superconducting magnet to create a strong, uniform, static magnetic field within a designated region (e.g., within a passage shaped to receive a patient). When a body of a patient (or portion of the body of the patient) is positioned within the magnetic field, nuclear spins associated with the hydrogen nuclei that form water within tissues of the patient become polarized. The magnetic moments associated with these spins become aligned along the direction of the magnetic field and result in a small net tissue magnetization in the direction of the magnetic field. MRI systems additionally include magnetic gradient coils that produce spatially-varying magnetic fields of smaller magnitudes relative to a magnitude of the uniform magnetic field resulting from the superconducting magnet. The spatially-varying magnetic fields are configured to be orthogonal to each other in order to spatially encode the region by creating a signature resonance frequency of the hydrogen nuclei at different locations in the body of the patient. Radio frequency (RF) coil assemblies are then used to create pulses of RF energy at or near the resonance frequency of the hydrogen nuclei. The pulses of RF energy are absorbed by the hydrogen nuclei, thereby adding energy to the nuclear spin system and adjusting the hydrogen nuclei from a rest state to an excited state. As the hydrogen nuclei relax back to the rest state from the excited state, they release the absorbed energy in the form of an RF signal. This signal is detected by the MRI system and is transformed into an image by a computer using known reconstruction algorithms.

In order to detect the RF signals emitted by the body of the patient, an RF coil assembly is often positioned proximate anatomical features to be imaged by the MRI system. An image quality of images produced by the MRI system is influenced by an ability of the RF coil assembly to closely conform to the contours of the body of the patient.

BRIEF DESCRIPTION

In one embodiment, a radio frequency (RF) coil assembly for a magnetic resonance imaging (MRI) system includes a flexible spine and at least two RF coil sections each coupled to the flexible spine and movable relative to each other. Each RF coil section comprises at least one flexible RF coil, with each RF coil including a loop portion comprising a coupling electronics portion and at least two parallel, distributed capacitance wire conductors encapsulated and separated by a dielectric material.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of systems and methods for a radio frequency (RF) coil assembly for magnetic resonance imaging (MRI). An MRI system, such as the MRI system shown by FIG. 1, includes a flexible RF coil assembly, such as the RF coil assembly shown by FIG. 2. The RF coil assembly includes several flexible sections joined to each other by a common flexible spine, with each of the sections including a plurality of RF coils as shown by FIG. 3. The flexible sections are pivotable relative to the flexible spine, as shown by FIGS. 4A-4D, in order to conform to the contours of the body of a patient, as shown by FIG. 5. Each of the sections may individually wrap around one or more anatomical features of the body of the patient in order to image the anatomical features via the MRI system. The RF coils are configured with coupling electronics and distributed capacitance wire conductors, as described with reference to FIGS. 6-12, such that each RF coil is transparent to each other RF coil. In this way, the sections of the RF coil assembly may be positioned against the body of the patient and wrapped around the patient in order to image portions of the body that include complicated geometries, such as the location at which the upper arms join to the torso. Because the RF coils include the coupling electronics and distributed capacitance wire conductors, the sections of the RF coil assembly may move and/or overlap relative to each other without degradation of MR signals transmitted to the MRI system by the RF coils.

Figure 1:
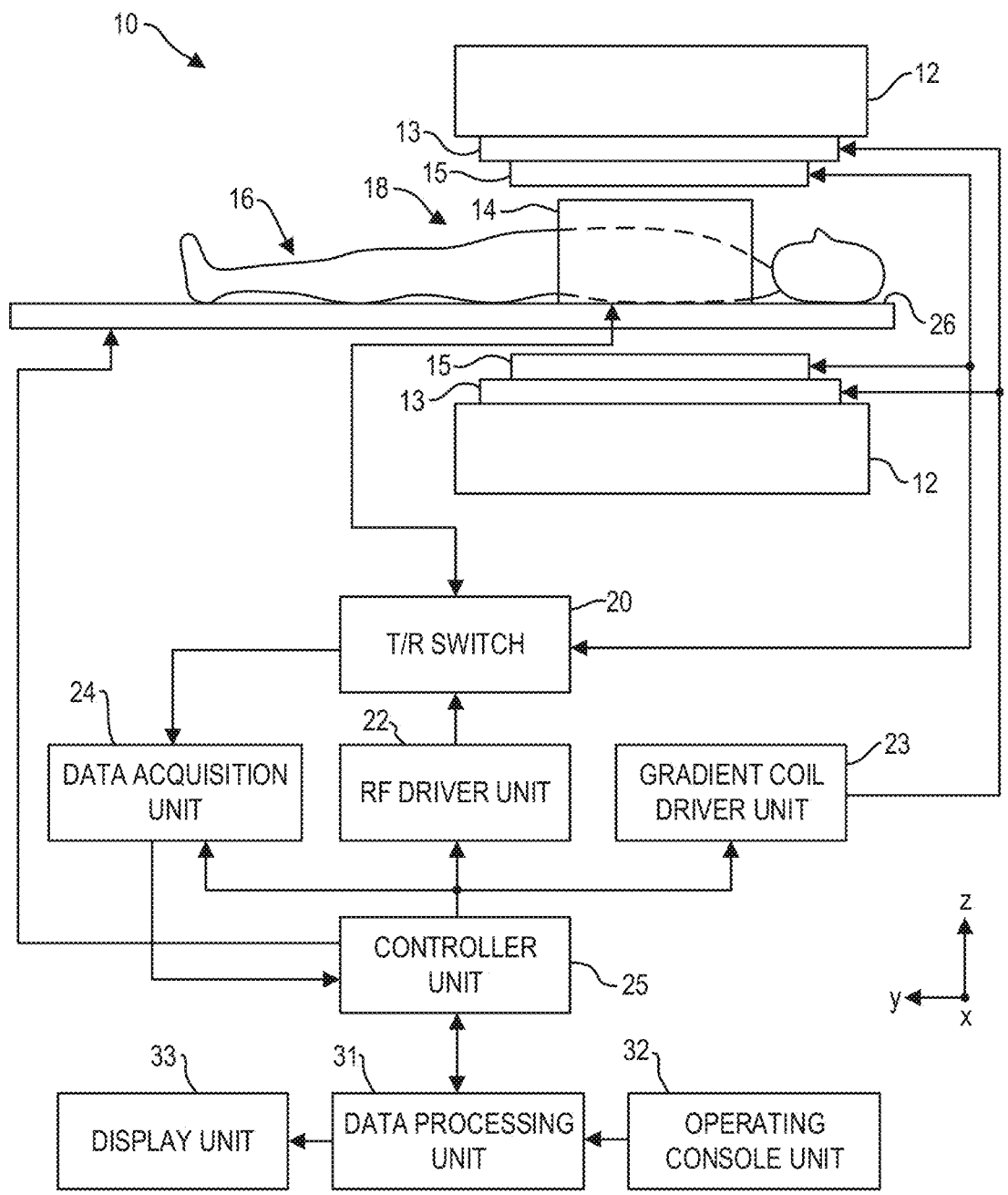
FIG. 1 schematically shows an MRI system including at least one RF coil, according to an embodiment.

Turning now to FIG. 1, a magnetic resonance imaging (MRI) apparatus 10 is shown. The MRI apparatus 10 includes a superconducting field magnet unit 12, a gradient coil unit 13, an RF coil unit 14 (which may be referred to herein as an RF coil assembly), an RF body or volume coil unit 15, a transmit/receive (T/R) switch 20, an RF driver unit 22, a gradient coil driver unit 23, a data acquisition unit 24, a controller unit 25, a patient table or bed 26, a data processing unit 31, an operating console unit 32, and a display unit 33. In one example, the RF coil unit 14 is a surface coil, which is a local coil that is typically placed proximate to the anatomy of interest of a subject 16 (e.g., a patient). Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are independent but electromagnetically coupled structures. The MRI apparatus 10 transmits electromagnetic pulse signals to the subject 16 placed in an imaging space 18 with a static magnetic field formed to perform a scan for obtaining magnetic resonance signals from the subject 16 to reconstruct an image of a slice of the subject 16 based on the magnetic resonance signals thus obtained by the scan.

The superconducting magnet unit 12 includes, for example, an annular superconducting magnet, which is mounted within a toroidal vacuum vessel. The magnet defines a cylindrical space surrounding the subject 16, and generates a constant, strong, uniform, static magnetic along the Z direction of the cylindrical space.

The MRI apparatus 10 also includes the gradient coil unit 13 that generates a gradient magnetic field in the imaging space 18 so as to provide the magnetic resonance signals received by the RF coil unit 14 with three-dimensional positional information. The gradient coil unit 13 includes three gradient coil systems, each of which generates a gradient magnetic field, which inclines into one of three spatial axes perpendicular to each other, and generates a gradient magnetic field in each of frequency encoding direction, phase encoding direction, and slice selection direction in accordance with the imaging condition. More specifically, the gradient coil unit 13 applies a gradient magnetic field in the slice selection direction of the subject 16, to select the slice; and the RF body coil unit 15 transmits an RF signal to a selected slice of the subject 16 and excites it. The gradient coil unit 13 also applies a gradient field in the phase encoding direction of the subject 16 to phase encode the magnetic resonance signals from the slice excited by the RF signal. The gradient coil unit 13 then applies a gradient magnetic field in the frequency encoding direction of the subject 16 to frequency encode the magnetic resonance signals from the slice excited by the RF signal.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field is formed by the superconducting magnet unit 12, the RF coil unit 14 transmits, based on a control signal from the controller unit 25, an RF signal that is an electromagnetic wave to the subject 16 and thereby generates a high-frequency magnetic field. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. The RF coil unit 14 may transmit and receive an RF signal using the same RF coil.

The RF body coil unit 15 is disposed, for example, to enclose the imaging space 18, and produces RF magnetic field pulses orthogonal to the main magnetic field produced by the superconducting field magnet unit 12 within the imaging space 18 to excite the nuclei. In contrast to the RF coil unit 14, which may be disconnected from the MR apparatus 10 and replaced with another RF coil unit, the RF body coil unit 15 is fixedly attached and connected to the MRI apparatus 10. Furthermore, whereas local coils such as those comprising the RF coil unit 14 can transmit to or receive signals from a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity, with relatively high RF power deposited in the subject in return. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode, a receive-only mode, or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coil unit 14 and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 14.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard, and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a slice image or three-dimensional (3D) image of the subject 16 generated by the data processing unit 31.

During a scan, RF coil-interfacing cables may be used to transmit signals between the RF coils (e.g., RF coil unit 14 and RF body coil unit 15) and other aspects of the processing system (e.g., data acquisition unit 24, controller unit 25, and so on), for example to control the RF coils and/or to receive information from the RF coils. As explained previously, the RF body coil unit 15 is a transmit coil that transmits RF signals, and the local surface RF coil 14 receives the MR signals. More generally, RF coils are used to transmit RF excitation signals ("transmit coil"), and to receive the MR signals emitted by an imaging subject ("receive coil"). In an example, the transmit and receive coils are a single mechanical and electrical structure or array of structures, with transmit/receive mode switchable by auxiliary circuitry. In other examples, the transmit body coil (e.g., RF body coil unit 15) and the surface receive coil (e.g., RF coil unit 14) may be independent structures that are physically coupled to each other via a data acquisition unit or other processing unit. For enhanced image quality, however, it may be desirable to provide a receive coil that is mechanically and electrically isolated from the transmit coil. In such case it is desirable that the receive coil, in its receive mode, be electromagnetically coupled to and resonant with an RF "echo" that is stimulated by the transmit coil. However, during transmit mode, it may be desirable that the receive coil is electromagnetically decoupled from and therefore not resonant with the transmit coil, during actual transmission of the RF signal. Such decoupling decreases a likelihood of noise being produced within the auxiliary circuitry when the receive coil couples to the full power of the RF signal. Additional details regarding the uncoupling of the receive RF coil will be described below.

Conventional RF coils may include acid etched copper traces (loops) on printed circuit boards (PCBs) with lumped electronic components (e.g., capacitors, inductors, baluns, resistors, etc.), matching circuitry, decoupling circuitry, and pre-amplifiers. Such a configuration is typically very bulky, heavy, and rigid, and requires relatively strict placement of the coils relative to each other in an array to prevent coupling interactions among coil elements that may degrade image quality. As such, conventional RF coils and RF coil arrays lack flexibility and hence may not conform to patient anatomy, degrading imaging quality and patient comfort.

Thus, according to embodiments disclosed herein, an RF coil assembly, such as RF coil unit 14, may include distributed capacitance wire conductors rather than copper traces on PCBs with lumped electronic components. As a result, the RF coil assembly may be lightweight and flexible, allowing placement in low cost, lightweight, waterproof, and/or flame retardant fabrics or materials. The coupling electronics portion coupling the loop portion of the RF coil (e.g., the distributed capacitance wire) may be miniaturized and utilize a low input impedance pre-amplifier, which is optimized for high source impedance (e.g., due to impedance matching circuitry) and allows flexible overlaps among coil elements in an RF coil array. Further, the RF coil-interfacing cable between the RF coils and system processing components may be flexible and include integrated transparency functionality in the form of distributed baluns, which allows rigid electronic components to be avoided and aids in spreading of the heat load.

The RF coil assembly may be structured for imaging specific anatomical features of a patient that are often difficult to image with rigid (e.g., inflexible) RF coil arrays. Specifically, the RF coil assembly may include at least two sections that are pivotable and/or bendable relative to each other, with each section being formed of a flexible material and including at least one flexible RF coil. In some examples (e.g., similar to the examples described below with reference to FIGS. 2-6), one or more of the sections may include two or more RF coils arranged to form an RF coil array. The RF coils of each section of the RF coil assembly are electrically coupled to each other and may output RF signals to a single output (e.g., a single coil-interfacing cable or cable harness) that is electrically coupleable to the MRI apparatus 10. Each of the sections may be wrapped around the anatomical feature of interest to be imaged by the MRI apparatus 10. For example, the different sections may be wrapped around an arm, shoulder, and neck of the patient in order to image the brachial plexus of the patient. Imaging the brachial plexus is often difficult with conventional RF coils due to the widely variable geometries of the arm, shoulder, and neck from patient to patient. In another example, the different sections may be wrapped around a thigh and groin of the patient in order to image the corresponding region of the body. The RF coil assembly disclosed herein may be fitted to a wide variety of patients of different sizes (e.g., weights, heights, etc.). Further, the RF coil assembly disclosed herein may increase a signal-to-noise ratio (SNR) of the images produced by the MRI apparatus 10 relative to conventional RF coils due to the ability of the sections of the RF coil assembly to wrap around the anatomy of the patient, enabling the RF coils to be positioned closer to the body of the patient. The ability of the RF coil assembly to fit to a wider variety of patients may decrease an imaging cost of the MRI apparatus 10 (e.g., by reducing a number of different RF coil assemblies utilized to image patients via the MRI apparatus 10) and may increase the imaging quality of the MRI apparatus 10 (e.g., by increasing the SNR).

Figure 2:
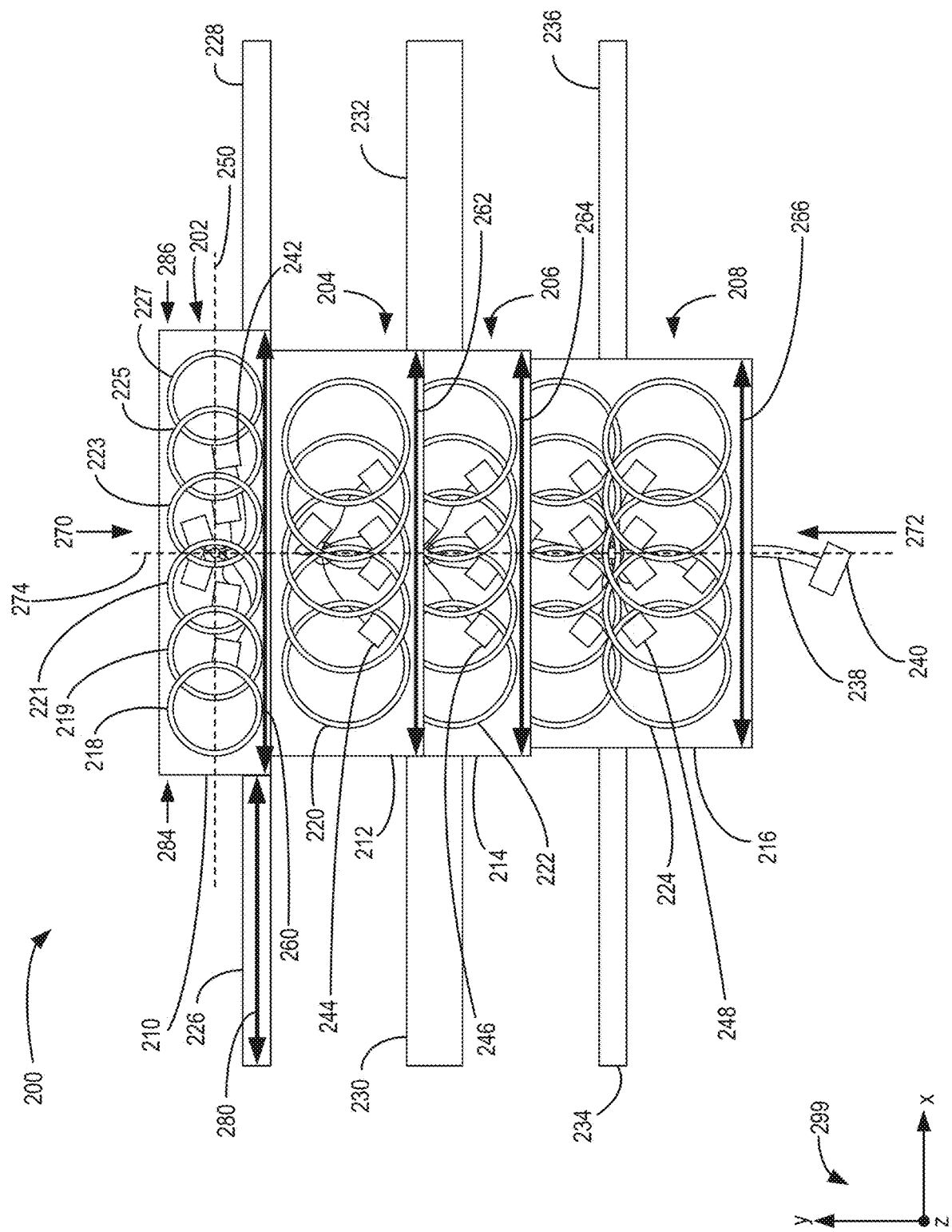
FIG. 2 shows a view of a first side of an RF coil assembly for an MRI system.
Figure 3:
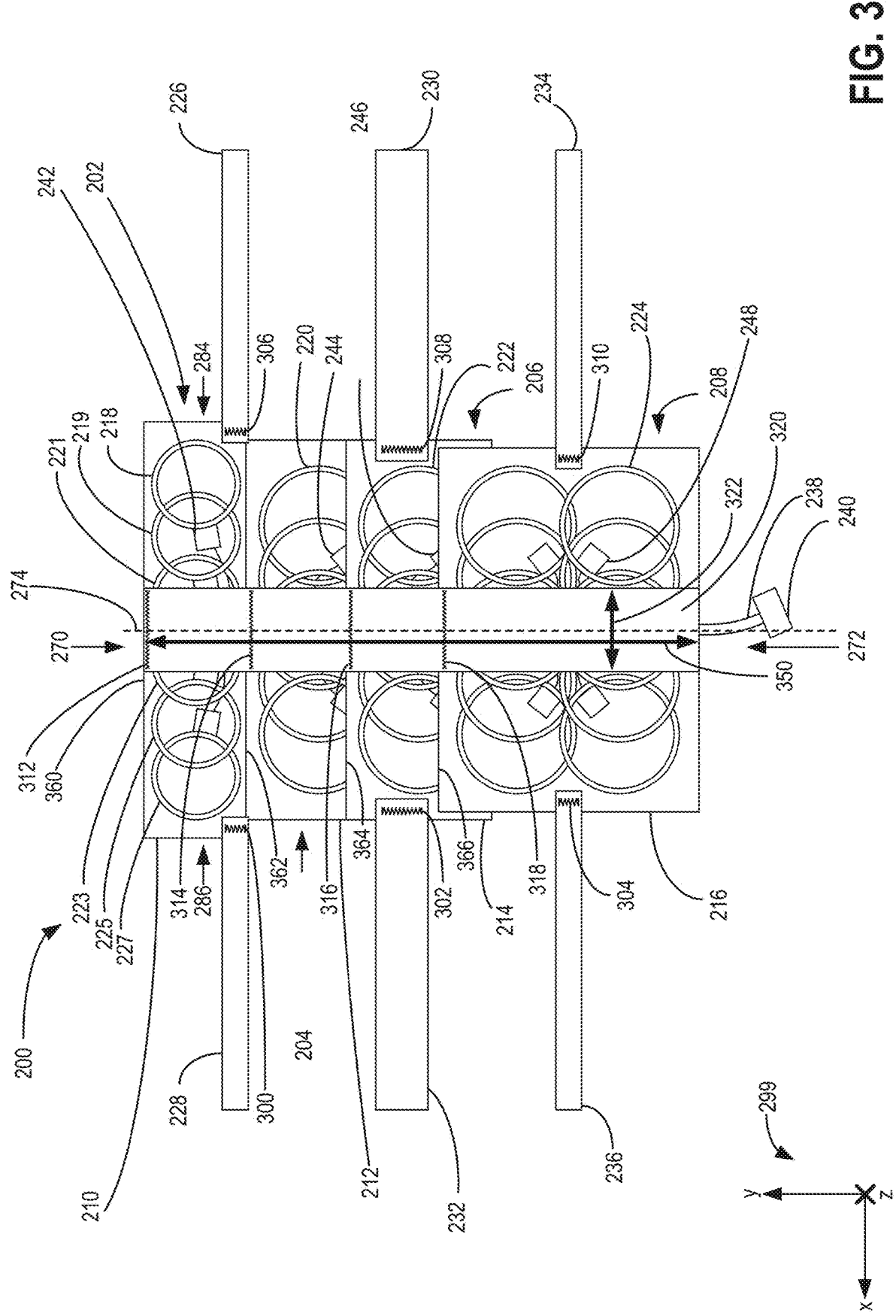
FIG. 3 shows a view of a second side of the RF coil assembly of FIG. 2.

Turning now to FIG. 2, a first view of RF coil assembly 200 is shown. RF coil assembly 200 may be similar to the RF coil unit 14 described above with reference to FIG. 1. For example, RF coil assembly 200 may be electrically coupled to an MRI apparatus (e.g., MRI apparatus 10 of FIG. 1 and described above) for imaging one or more anatomical features of a patient. In one example, RF coil assembly 200 may be utilized in order to image the brachial plexus and/or torso of a patient, as described further below. In another example, RF coil assembly 200 may be utilized to image a lower region of the patient, such as a region of the thigh, hip, and/or groin.

The RF coil assembly 200 includes at least two flexible sections that are pivotable and/or bendable relative to each other. The sections are moveable relative to each other and are arranged to overlap each other such that the RF coil assembly 200 may resemble a piece of armor. Specifically, the RF coil assembly 200 includes first section 210, second section 212, third section 214, and fourth section 216, with the second section 212 overlapping the third section 214, and with the third section 214 overlapping the fourth section 216. Each of the sections is moveable (e.g., rotatable, pivotable, bendable, etc.) relative to each other section. The first section 210, second section 212, third section 214, and fourth section 216 may each be referred to herein as RF coil sections and/or RF coil array sections. In the example shown by FIG. 2, the first section 210 does not overlap the second section 212. However, in other examples, the first section 210 may overlap the second section 212. In some examples, one or more edges of the sections may overlap one or more edges of adjacent sections. Further, one or more edges of RF coils of each section (e.g., RF coil arrays) may overlap with one or more edges of RF coils of other sections (e.g., other RF coil arrays). For example, a bottom edge of the second section 212 (e.g., an edge of the second section 212 positioned closest to second end 272) may overlap a top edge of the third section 214 (e.g., top edge 364 shown by FIG. 3), and a bottom edge of the third section 214 (e.g., an edge of the third section positioned closest to second end 272) may overlap with a top edge of the fourth section 216 (e.g., top edge 366 shown by FIG. 3).

Each of the sections of the RF coil assembly 200 may wrap around the body of the patient at a different location of the body. For example, first section 210 may cover (e.g., wrap around) a neck of the patient (e.g., in order to image the neck via an MRI apparatus, such as MRI apparatus 10 shown by FIG. 1 and described above), second section 212 may cover (e.g., wrap around) a shoulder of the patient, third section 214 may cover (e.g., wrap around) an upper portion (e.g., upper section) of an arm of the patient, and fourth section 216 may cover (e.g., wrap around) a lower portion (e.g., lower section) of the arm of the patient. In some examples, one or more of the sections may wrap around a same anatomical feature of the body. For example, second section 212 and third section 214 may each wrap around a corresponding portion of the shoulder of the patient, and the second section 212 and third section 214 may overlap along the shoulder. Although the RF coil assembly 200 is shown including four sections (e.g., first section 210, second section 212, third section 214, and fourth section 216), in other examples the RF coil assembly 200 may include a different number of sections (e.g., five sections, six sections, etc.).

The RF coil assembly 200 may be utilized to image multiple anatomical features of the patient without repositioning of the RF coil assembly 200 relative to the body of the patient. For example, an operator of the MRI apparatus (which may be referred to herein as an MRI system) may couple the RF coil assembly 200 to the body of the patient in order to image the brachial plexus, torso, and long bones of the arm (e.g., humerus and/or radius) with a single scan of the MRI system (e.g., without performing multiple scans or imaging operations via the MRI system and without moving the RF coil assembly 200 relative to the body of the patient). In other examples, the operator may image other anatomical features of the body of the patient via the RF coil assembly 200, such as the heart, lungs, and/or the C-spine/upper thoracic region.

Each section of the RF coil assembly 200 may be sized according to the anatomical feature to be imaged. For example, first section 210 may be sized to wrap around a neck of a patient, second section 212 may be sized to wrap around and/or drape across a shoulder of the patient, third section 214 may be sized to wrap around an upper arm of the patient, and fourth section 216 may be sized to wrap around a portion of each of the upper arm and lower arm of the patient. In particular, the first section 210 may be sized such that a length 260 of the first section 210 is slightly larger (e.g., within a range of 3 centimeters to 10 centimeters larger) than a circumference of a neck of an average-sized patient (e.g., a patient of average height and/or weight within a population or country). For example, an average American woman may have a height of 162 centimeters and a neck circumference of 35 centimeters, and the length 260 of the first section 210 may be between 38 centimeters and 45 centimeters. The other sections of the RF coil assembly 200 (e.g., second section 212, third section 214, and fourth section 216) are sized in a similar way according to the average size of the anatomical features to be imaged by each section. For example, a length 262 of the second section 212 may be sized according to a shoulder size of the average patient such that the length 262 is slightly greater than the average shoulder size (e.g., within a range of 3 centimeters to 10 centimeters larger than the average shoulder size), a length 264 of the third section 214 may be sized according to an upper arm circumference of the average patient (e.g., slightly larger than the average upper arm circumference), and a length 266 of the fourth section 216 may be sized according to a lower arm circumference of the average patient (e.g., slightly larger than the average lower arm circumference).

In FIG. 2, the RF coil assembly 200 is shown in a flattened configuration such that each section lies approximately along the same plane (e.g., a configuration in which the RF coil assembly 200 is not coupled to the body of a patient and the first section 210, second section 212, third section 214, and fourth section 216 are not wrapped as described above). Each of the sections includes at least one flexible RF coil, and in some examples one or more of the sections may include a plurality of RF coils arranged to form an RF coil array. Specifically, in the example shown by FIG. 2, first section 210 includes first coil array 202 comprising a plurality of RF coils, second section 212 includes second coil array 204 comprising a plurality of RF coils, third section 214 includes third coil array 206 comprising a plurality of RF coils, and fourth section 216 includes fourth coil array 208 comprising a plurality of RF coils. In some examples, the RF coils of the RF coil arrays may be arranged along a same axis. For example, the first coil array 202 includes first RF coil 218, second RF coil 219, third RF coil 221, fourth RF coil 223, fifth RF coil 225, and sixth RF coil 227, with each of the RF coils centered along axis 250 (which may be referred to herein as a longitudinal axis of first section 210) extending parallel to length 260, and with the axis 250 being perpendicular to central axis 274. In other examples, the RF coils may be positioned in a different relative arrangement (e.g., not aligned along a same axis). However, by aligning the RF coils of the first section 210 along axis 250, the first section 210 may be utilized to image an entire the neck of the patient to which the RF coil assembly 200 is coupled. For example, the RF coils of the first coil array 202 overlap with each other along axis 250, and during conditions in which the first section 210 is wrapped around the neck of the patient, each portion of the neck is proximate to (e.g., encircled by) at least one of the RF coils of the first coil array 202 such that the entire neck may be imaged by the MRI system via the first section 210.

In some examples, at least one of the first section 210, second section 212, third section 214, and fourth section 216 may include exactly one RF coil. For example, second section 212, third section 214, and fourth section 216 may each include more than one RF coil, and first section 210 may include exactly one RF coil and no other RF coils. In another example, first section 210 may include exactly one RF coil and no other RF coils, second section 212 may include exactly one RF coil and no other RF coils, and third section 214 and fourth section 216 may each include more than one RF coil. Other examples are possible.

The RF coils of each section may have different dimensions (e.g., different diameters) relative to each other section. For example, the RF coils of the first section 210 may have a diameter of 8 cm, and the RF coils of the second section may have a diameter of 11 cm. Further, in some examples, one or more RF coils within a same section may have different dimensions (e.g., different diameters) relative to other RF coils within the same section. For example, first RF coil 218 of first section 210 may have a diameter of 8 cm, and second RF coil 219 of first section 210 may have a diameter of 9 cm. Other examples are possible.

Although the configuration of the RF coils of the first coil array 202 and first section 210 is described above as an example, each other section of the RF coil assembly 200 (e.g., second section 212, third section 214, and fourth section 216) may be configured in a similar way. For example, the RF coils of the second coil array 204 may be arranged along an axis of the second section 212 (e.g., an axis parallel to length 262), the RF coils of the third coil array 206 may be arranged along an axis of the third section 214 (e.g., an axis parallel to length 264), etc. Further, in some examples, one or more of the sections may include multiple rows of RF coils (e.g., as shown with the fourth coil array 208 of fourth section 216), with the RF coils of each row arranged along a corresponding axis (e.g., an axis parallel to length 266, with respect to the example of fourth section 216).

Each of the sections of the RF coil assembly 200 (e.g., first section 210, second section 212, third section 214, and fourth section 216) may be formed of a flexible material that is transparent to RF signals. In one example, the sections of the RF coil assembly 200 may be formed of one or more layers of Nomex® material. The RF coils of each section may be embedded within the flexible material in some examples (e.g., fully enclosed by one or more layers of the flexible material). An example of the RF coils of the first section 210 embedded within the first section 210 is shown by the cross-sectional view of FIG. 6 along axis 250. Further, each RF coil is coupled to corresponding coupling electronics (e.g., coupling electronics portions 242 coupled to sixth RF coil 227), and the corresponding coupling electronics (and the electrical wires coupled to the coupling electronics and/or RF coils) may be embedded within the flexible material along with the RF coils. For example, coupling electronics portion 244 of an RF coil of the second section 212 (e.g., an RF coil of the second coil array 204) may be embedded within the material of second section 212, coupling electronics portion 246 of an RF coil of the third section 214 (e.g., an RF coil of the third coil array 206) may be embedded within the material of third section 214, and coupling electronics portion 248 an RF coil of the fourth section 216 (e.g., an RF coil of the fourth coil array 208) may be embedded within the material of fourth section 216. In other examples, the RF coils, coupling electronics, and/or electrical wires may be removably coupled (e.g., mounted) to each section. The RF coils may bend and/or deform along with the flexible material without degradation of signals (e.g., RF signals) associated with the RF coils (e.g., signals used to image the patient with the MRI system via the RF coil assembly, as described above).

Figure 6:
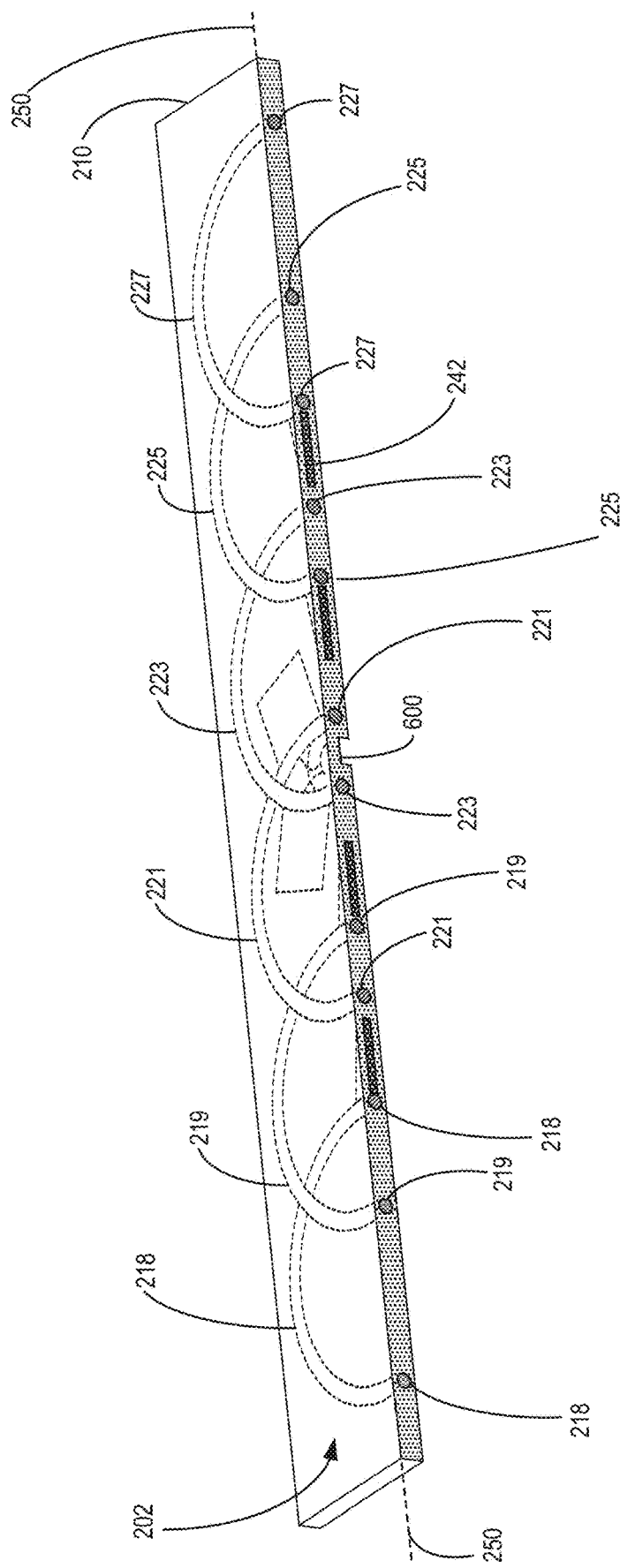
FIG. 6 shows a cross-sectional view of an RF coil array of the RF coil assembly of FIGS. 2-5.

Although the RF coils of the first section 210 (e.g., first coil array 202), second section 212 (e.g., second coil array 204), third section 214 (e.g., third coil array 206), and fourth section 216 (e.g., fourth coil array 208) are shown by FIGS. 2-3, the RF coils may be embedded within the material of the corresponding sections of the RF coil assembly as described above and may not be visible to an observer (e.g., not visible to the patient and/or operator). The RF coils are shown by FIGS. 2-3 in order to illustrate a relative positioning and arrangement of the RF coils with respect to the first section 210, second section 212, third section 214, and fourth section 216. An example of the RF coils of the first section 210 embedded within the material of the first section 210 is shown by FIG. 6 and described further below.

The RF coil assembly 200 includes a coil-interfacing cable 238 (which may be referred to herein as a cable harness) having a connector 240. Each of the electrical wires coupled to the coupling electronics portions (e.g., coupling electronics portions 242, 244, etc.) may be housed together (e.g., bundled together) within the coil-interfacing cable 238 and electrically coupled to the connector 240. For example, as shown by FIG. 6, first section 210 may include a port 600 through which the electrical wires may extend outward from the first section 210 to join with the coil-interfacing cable 238. Each section may include a similar port (e.g., similar to port 600 shown by FIG. 6), and the coil-interfacing cable 238 may be electrically coupled with the wires coupled to the coupling electronics portions via each port in some examples. The coil-interfacing cable 238 extends between each coupling electronics portion and the connector 240 (which may be referred to herein as an RF coil interfacing connector). Connector 240 may interface with the MRI system (e.g., electrically couple with the MRI system by plugging into an input of the MRI system) in order to output signals from the RF coils to the MRI system, and the MRI system may process the signals received from the RF coils of the RF coil assembly 200 via the connector in order to produce images of the body of the patient (e.g., images of the anatomical features of the patient to be imaged by the RF coil assembly 200). In the examples shown, the coil-interfacing cable 238 extends outward from a second end 272 of the RF coil assembly 200, with the second end 272 being opposite to a first end 270 along central axis 274 of the RF coil assembly 200, and with the first section 210 being positioned at the first end 270 and the fourth section 216 being positioned at the second end 272.

The RF coil assembly 200 includes a plurality of straps configured to couple the RF coil assembly 200 to the body of the patient. Specifically, the first section 210 includes first strap 226 and second strap 228, the third section 214 includes third strap 230 and fourth strap 232, and the fourth section 216 includes fifth strap 234 and sixth strap 236. The first strap 226 is positioned opposite to the second strap 228 relative to central axis 274, the third strap 230 is positioned opposite to the fourth strap 232 relative to central axis 274, and the fifth strap 234 is positioned opposite to the sixth strap 236 relative to central axis 274. The first strap 226 and second strap 228 are positioned at opposing sides of the first section 210 such that the first strap 226 and second strap 228 may couple together across the body of the patient (e.g., wrap around the body of the patient in order to secure the RF coil assembly 200 to the patient). Similarly, third strap 230 and fourth strap 232 are positioned at opposing sides of the third section 214 such that the third strap 230 and fourth strap 232 may couple together across the body of the patient, and fifth strap 234 and sixth strap 236 are positioned at opposing sides of the fourth section 216 such that the fifth strap 234 and sixth strap 236 may couple together across the body of the patient. An example of the RF coil assembly 200 coupled to the body of the patient is shown by FIG. 5 and described further below.

Although the RF coil assembly 200 is described above as including the first strap 226, second strap 228, third strap 230, fourth strap 232, fifth strap 234, and sixth strap 236, in other examples the RF coil assembly 200 may include a different number, size, and/or arrangement of straps. For example, the RF coil assembly 200 may include only the first strap 226, third strap 230, and fifth strap 234, with a length of each of the first strap 226, third strap 230, and fifth strap 234 being greater than the lengths shown by FIGS. 2-3 (e.g., a length of the first strap 226 may be twice the length 280 shown by FIG. 2, and the lengths of the third strap 230 and fifth strap 234 may be sized similarly relative to the first strap 226). In such examples, the first strap 226, third strap 230, and fifth strap 234 may each wrap around the body of the patient and may couple to the one or more fasteners (e.g., buckles, hook and loop fasteners, etc.) positioned opposite to the first strap 226, third strap 230, and fifth strap 234 relative to central axis 274. For example, first strap 226 is positioned at first side 284 of the first section 210, and one or more fasteners may be coupled to the first section 210 at an opposing, second side 286 of the first section 210. The first strap 226 may wrap around the body of the patent and couple with the one or more fasteners at the second side 286 in order to couple the RF coil assembly 200 to the patient. In other examples, the first side 284 may include one or more fasteners adapted to couple with the second strap 228 in a similar way. Further, other sections (e.g., second section 212, third section 214, and/or fourth section 216) may include fasteners adapted to couple with the corresponding straps of the sections, similar to the example of the first strap 226 described above.

Turning now to FIG. 3, a second view of the RF coil assembly 200 is shown, with the RF coil assembly 200 in the flattened configuration. The view shown by FIG. 3 is opposite to the view shown by FIG. 2. Specifically, FIG. 2 shows a view of a front side of the RF coil assembly 200 (e.g., with the front side facing away from the patient during conditions in which the RF coil assembly 200 is coupled to the patient), and FIG. 3 shows a view of a rear side of the RF coil assembly 200 (e.g., with the rear side facing toward the patient during conditions in which the RF coil assembly 200 is coupled to the patient). FIGS. 2-3 each include reference axes 299 for comparison of the views shown. With regard to FIG. 2, the z-axis of reference axes 299 extends out of the page (e.g., out of a plane of the view of FIG. 2 and in an outward direction from the front side of the RF coil assembly 200). With regard to FIG. 3, the z-axis of reference axes 299 extends into the page (e.g., into a plane of the view of FIG. 3).

As shown by FIG. 3, the RF coil assembly 200 includes a flexible spine 320. Flexible spine 320 extends in a direction of the central axis 274, and the flexible spine 320 is centered along the central axis 274. Specifically, central axis 274 extends in a perpendicular direction relative to a width 322 of the flexible spine 320, with the width 322 being parallel to the x-axis of reference axes 299 and with the central axis 274 being parallel to the y-axis of reference axes 299, and with the x-axis and y-axis arranged perpendicular to each other. Width 322 may be less than half of length 260.

The flexible spine 320 is coupled to each of the sections of the RF coil assembly 200 via corresponding connections. Specifically, first section 210 is coupled to flexible spine 320 by connection 312, second section 212 is coupled to flexible spine 320 by connection 314, third section 214 is coupled to flexible spine 320 by connection 316, and fourth section 216 is coupled to flexible spine 320 by connection 318. In one example, the connections 312, 314, 316, and 318 may be stitching. For example, first section 210 may be stitched (e.g., sewn) to the flexible spine 320 at connection 312, second section 212 may be stitched to the flexible spine 320 at connection 314, etc. In another example, the connections 312, 314, 316, and 318 may be a different type of coupling between the flexible spine 320 and the corresponding sections. For example, first section 210 may be fused (e.g., RF welded), adhered (e.g., glued), and/or fastened (e.g., staple, tied, coupled via hook and loop fasteners, etc.) to the flexible spine 320 at connection 312. Second section 212, third section 214, and fourth section 216 may be coupled to the flexible spine 320 via their corresponding connections (e.g., connections 314, 316, and 318, respectively) in a similar way.

Each of the connections 312, 314, 316, and 318 may utilize the flexibility of the material of the flexible spine 320 and the sections 210, 212, 214, and 216 to enable the sections to move (e.g., pivot, twist, rotate, etc.) relative to the flexible spline 320 and relative to each other. Specifically, in some examples, the connections 312, 314, 316, and 318 may not include any additional components such as pins, shafts, sockets, bearings, journals, holes, hinges, etc. to provide rotational degrees of freedom to the sections 210, 212, 214, and 216. Instead, the rotational degrees of freedom of the sections 210, 212, 214, and 216 are provided solely by the material of the sections 210, 212, 214, and 216. Each section is fixed to the flexible spine 320 by its corresponding connection, with the connections not including any components that rotate relative to the flexible spine or the sections 210, 212, 214, and 216

At least two of the sections of the RF coil assembly 200 are only coupled to each other via the flexible spine 320 (e.g., are not fixedly coupled to each other and are moveable relative to each other) and are not directly coupled to each other at any location. Specifically, although the first section 210, second section 212, third section 214, and fourth section 216 may partially overlap each other (e.g., second section 212 may partially overlap third section 214, third section 214 may partially overlap fourth section 216, etc.) and are each directly coupled to the flexible spine 320, at least two of the sections are not directly coupled to each other. Directly coupling includes fixedly coupling via fusing, fastening, adhering, etc. as described above with reference to connections 312, 314, 316, and 318. Directly coupling does not include positioning the sections in contact with each other without fastening, fusing, etc. the sections to each other. Further, directly coupling does not include maintaining the sections in contact with each other via only friction.

Although the first section 210, second section 212, third section 214, and fourth section 216 may be referred to herein as coupled to each other via the flexible spine 320, the sections are not directly coupled to each other as defined above. Specifically, first section 210 is directly coupled to the flexible spine 320 via connection 312 and is not directly coupled to the second section 212, third section 214, or fourth section 216. Second section 212 is directly coupled to the flexible spine 320 via connection 314 and is not directly coupled to the first section 210, third section 214, or fourth section 216. Third section 214 is directly coupled to the flexible spine 320 via connection 314 and is not directly coupled to the first section 210, second section 212, or fourth section 216. Fourth section 216 is directly coupled to the flexible spine 320 via connection 316 and is not directly coupled to the first section 210, second section 212, or third section 214. In this configuration, the four sections of the RF coil assembly 200 are arranged in an overlapping or semi-lapping manner along the central axis 274, with the central axis 274 defined by the flexible spine 320 (e.g., central axis 274 extends along length 350 of the flexible spine 320 and is centered with respect to the flexible spine 320 as described above, with the length 350 perpendicular to the width 322 and parallel to the y-axis of reference axes 299).

Each of the straps of the RF coil assembly 200 (e.g., first strap 226, second strap 228, third strap 230, fourth strap 232, fifth strap 234, and sixth strap 236) may be directly coupled to corresponding sections of the RF coil assembly 200. Specifically, first strap 226 may be directly coupled to first section 210 via connection 306, second strap 228 may be directly coupled to first section 210 via connection 300, third strap 230 may be directly coupled to third section 214 via connection 308, fourth strap 232 may be directly coupled to third section 214 via connection 302, fifth strap 234 may be directly coupled to fourth section 216 via connection 310, and sixth strap 236 may be directly coupled to fourth section 216 via connection 304.

In the examples shown, the first section 210 is directly coupled to the flexible spine 320 only by the connection 312, with the connection 312 positioned at top edge 360 of the first section 210. The second section 212 is directly coupled to the flexible spine 320 only by the connection 314, with the connection 314 positioned at top edge 362 of the second section 212. The third section 214 is directly coupled to the flexible spine 320 only by the connection 316, with the connection 316 positioned at top edge 364 of the third section 214. The fourth section 216 is directly coupled to the flexible spine 320 only by the connection 318, with the connection 318 positioned at top edge 366 of the fourth section 216. In this way, each of the RF coil sections may be fixedly coupled to the flexible spine only along a top edge of the respective section. For example, first section 210 may only be fixedly coupled to flexible spine 320 at a top edge of first section 210, and first section 210 may not be fixedly coupled to flexible spine 320 at a bottom edge of first section 210. Each connection may have a top terminating edge and a bottom terminating edge where fixed coupling to the flexible spine ends, and each section may not be coupled to the flexible spine at any point above the top terminating edge and below the bottom terminating edge.

The RF coil assembly 200 is configured to be interchangeably couplable with either of the left arm or right arm of the patient. Specifically, the arrangement of the sections of the RF coil assembly 200 with respect to the flexible spine 320 enables the RF coil assembly 200 to be coupled to either arm of the patient. For example, the RF coil assembly 200 may be coupled to the left arm of the patient and the left arm may be imaged by the MRI apparatus. The RF coil assembly may then be decoupled from the left arm and coupled to the right arm, and the right arm may be imaged by the MRI apparatus. In this configuration, both arms of the patient may be imaged by the RF coil assembly 200 without additional RF coils, RF coil assemblies, and/or RF coil arrays.

Each of the sections (e.g., first section 210, second section 212, third section 214, and fourth section 216) may be centered relative to the flexible spine 320 to increase an ease with which the RF coil assembly 200 is coupled to either of the left arm or right arm of the patient. For example, the sections may be directly coupled to the flexible spine 320 in positions such that the central axis 274 bisects each of the lengths 260, 262, 264, and 266 shown by FIG. 2.

In this configuration, a position of the RF coil assembly 200 during conditions in which the RF coil assembly 200 is coupled to the left arm of the patient may be a mirror image of a position of the RF coil assembly during conditions in which the RF coil assembly 200 is coupled to the right arm of the patient. Specifically, first section 210 may wrap around the neck of the patient during conditions in which the RF coil assembly 200 is coupled to a left side (e.g., left arm) or right side (e.g., right arm) of the patient, second section 212 may wrap around the left shoulder during conditions in which the RF coil assembly 200 is coupled to the left side of the patient and second section 212 may wrap around the right shoulder during conditions in which the RF coil assembly 200 is coupled to the right side of the patient, and third section 214 and fourth section 216 may each wrap around the left arm during conditions in which the RF coil assembly is coupled to the left side of the patient or the right arm during conditions in which the RF coil assembly is coupled to the right side of the patient. Further, during conditions in which the RF coil assembly is utilized to image a lower region of the patient as described above, the RF coil assembly may couple to features at the left side of the patient (e.g., the left thigh, hip, and/or groin) or may couple to features at the right side of the patient (e.g., the right thigh, hip, etc.), with the position of the RF coil assembly 200 at the left side of the patient during conditions in which the RF coil assembly 200 is coupled to the left side being a mirror image of the position of the RF coil assembly 200 at the right side of the patient during conditions in which the RF coil assembly 200 is coupled to the right side.

An example of the RF coil assembly 200 coupled to a patient 500 is shown by FIG. 5. First section 210 is shown wrapped around neck 508 of the patient 500, with second section 212 positioned over the shoulder of right arm 502, and with third section 214 and fourth section 216 wrapped around the right arm 502. Fourth strap 232 couples across torso 506 of the patient in order to maintain a position of the RF coil assembly 200 relative to the body of the patient. As described above, during conditions in which the RF coil assembly 200 is coupled to left arm 504, the position of the RF coil assembly 200 is a mirror image of the position of the RF coil assembly 200 during conditions in which the RF coil assembly 200 is coupled to the right arm 502. A position of the RF coil assembly 200 during conditions in which the RF coil assembly 200 is coupled to the left arm 504 is indicated by dotted outline 520.

Figure 4A:
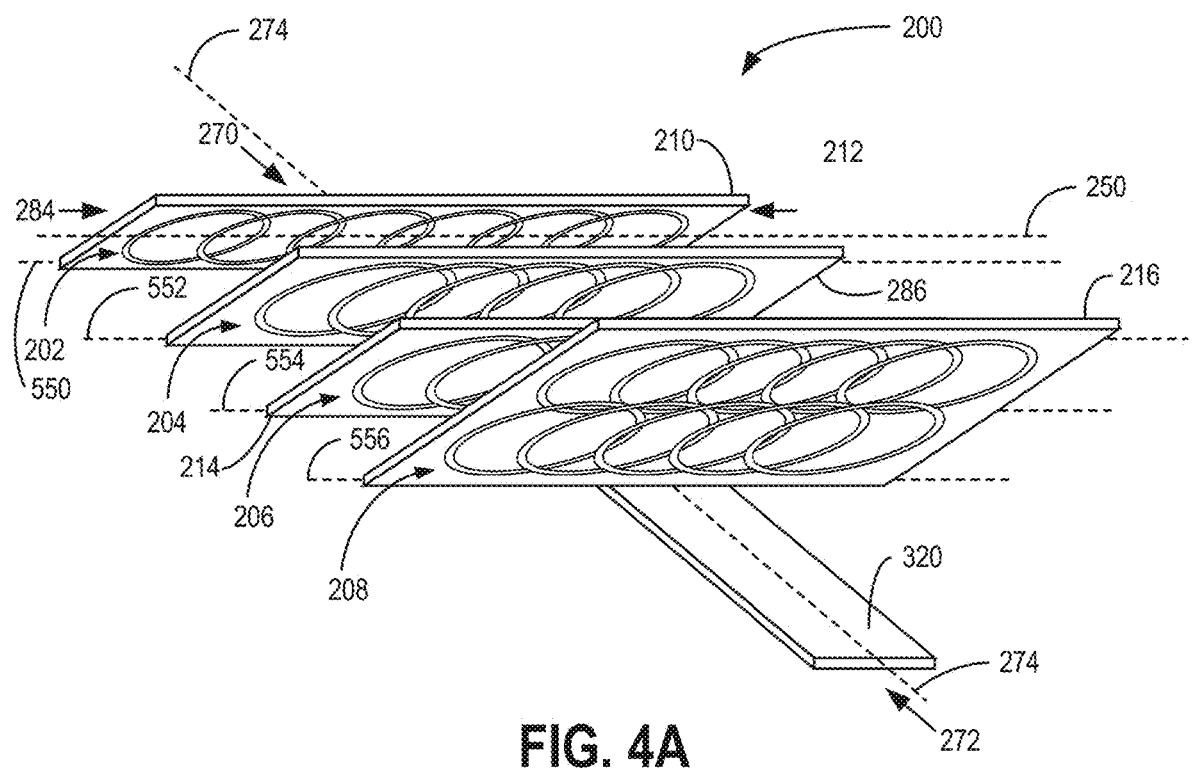
FIGS. 4A-4D show views of the RF coil assembly of FIGS. 2-3 with sections of the RF coil assembly in different angled positions.
Figure 4B:
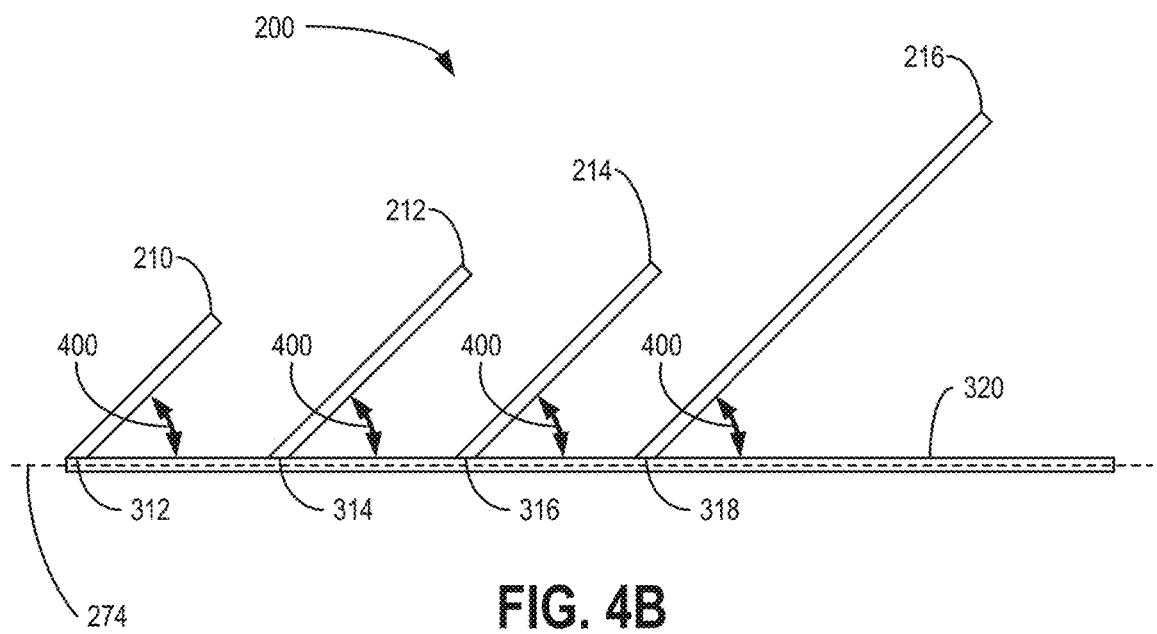
Figure 4C:
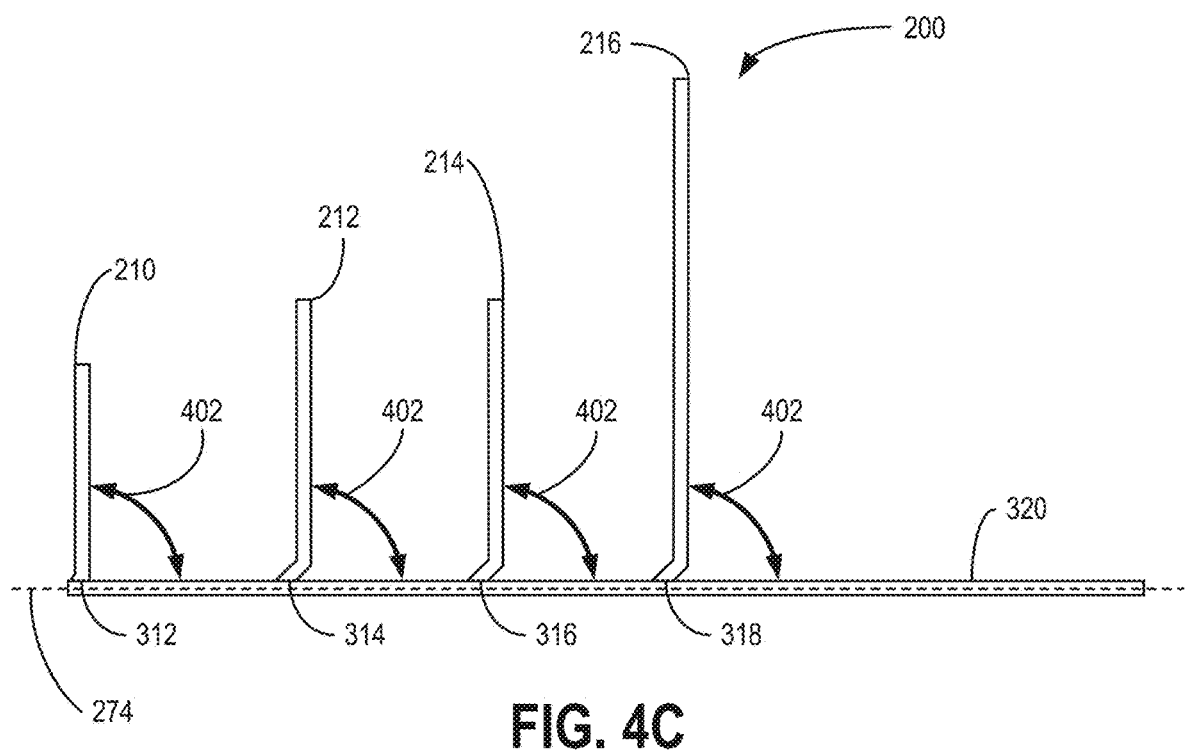
Figure 4D:
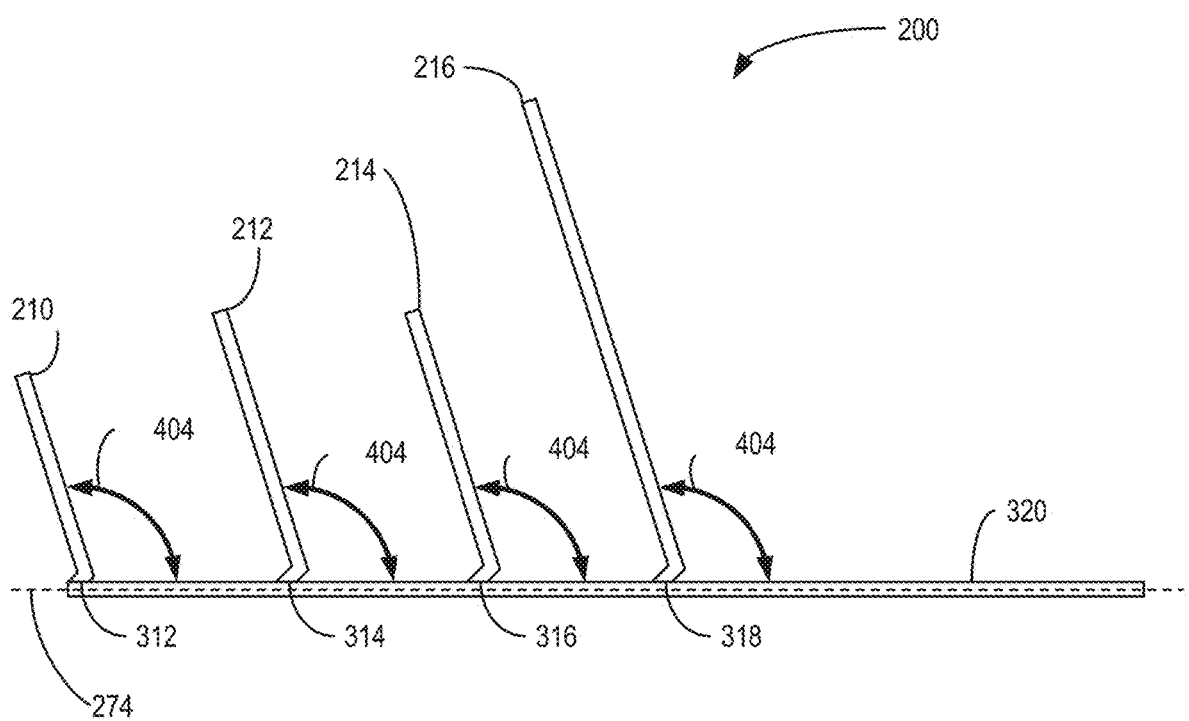
Figure 5:
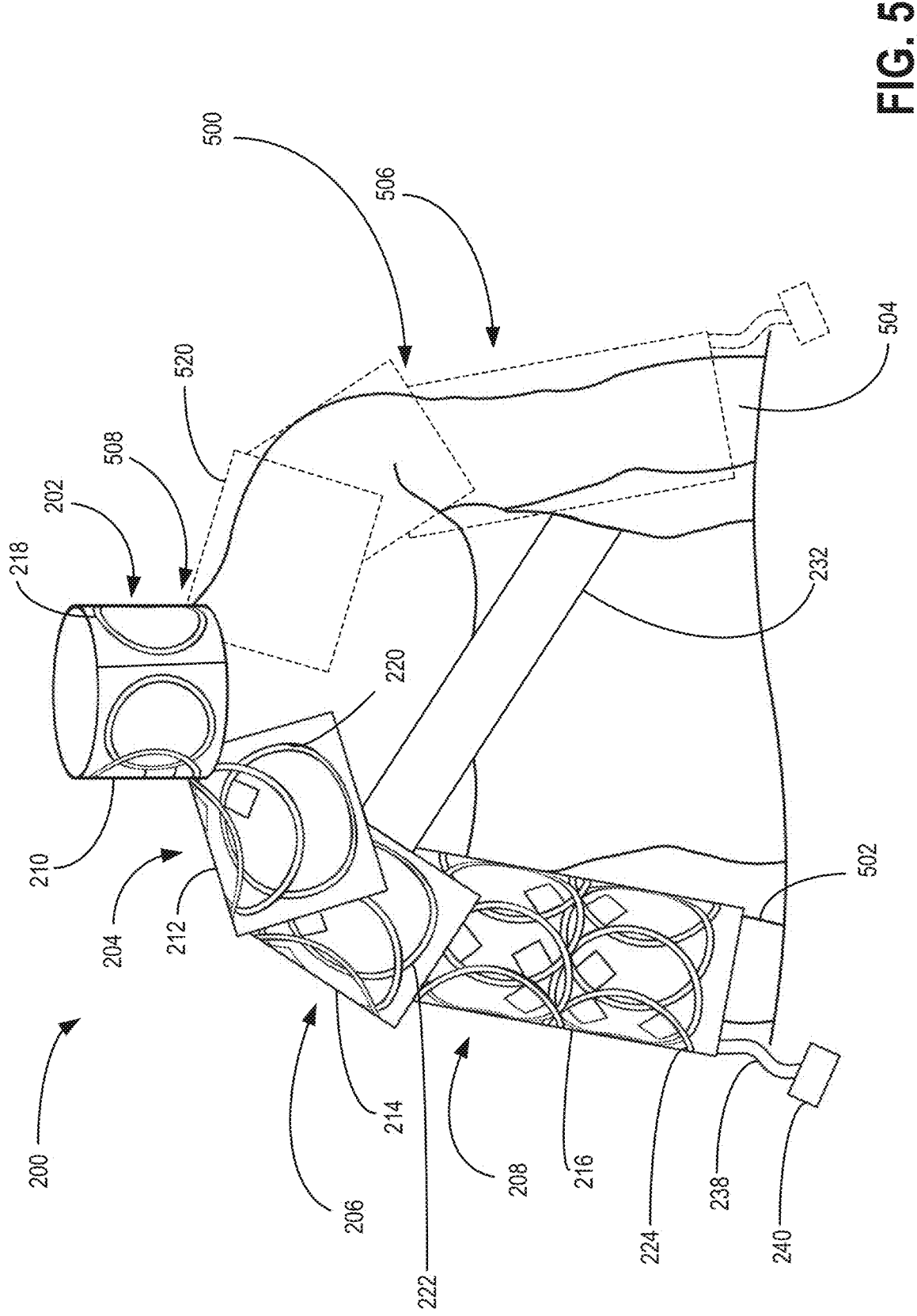
FIG. 5 shows a front view of the RF coil assembly of FIGS. 2-4, with the RF coil assembly coupled to a body of a patient.

Turning to FIGS. 4A-4D, each of the figures shows the RF coil assembly 200 with the sections in angled (e.g., pivoted, rotated, etc.) positions. Specifically, FIG. 4A shows a perspective view of the RF coil assembly 200 with the sections (e.g., first section 210, second section 212, third section 214, and fourth section 216) angled relative to flexible spine 320 by a first amount, FIG. 4B shows a side view of the configuration shown by FIG. 4A, FIG. 4C shows a side view of the RF coil assembly 200 with the sections angled by a second amount, and FIG. 4D shows a side view of the RF coil assembly 200 with the sections angled by a third amount. Specifically, in each of the views shown by FIGS. 4A-4D, the sections are angled relative to the central axis 274 such that each section is not parallel with the flexible spine 320.

In FIGS. 4A-4B, the sections are angled relative to the flexible spine 320 by angle 400 (shown by FIG. 4B) around respective axes (e.g., first section 210 is angled by angle 400 around axis 550, second section 212 is angled by angle 400 around axis 552, third section 214 is angled by angle 400 around axis 554, and fourth section 216 is angled by angle 400 around axis 556, with axes 550, 552, 554, and 556 shown by FIG. 4A, and with the sections angled in an upward direction away from flexible spine 320). In FIG. 4C, the sections are angled relative to the flexible spine 320 by angle 402 (e.g., first section 210 is angled by angle 402 around axis 550, second section 212 is angled by angle 402 around axis 552, third section 214 is angled by angle 402 around axis 554, and fourth section 216 is angled by angle 402 around axis 556, with axes 550, 552, 554, and 556 shown by FIG. 4A, and with the sections angled in an upward direction away from flexible spine 320). In FIG. 4D, the sections are angled relative to the flexible spine 320 by angle 404 (e.g., first section 210 is angled by angle 404 around axis 550, second section 212 is angled by angle 404 around axis 552, third section 214 is angled by angle 404 around axis 554, and fourth section 216 is angled by angle 404 around axis 556, with axes 550, 552, 554, and 556 shown by FIG. 4A, and with the sections angled in an upward direction away from flexible spine 320). In one example, angle 400 may be less than 90 degrees relative to central axis 274, angle 402 may be 90 degrees relative to central axis 274, and angle 404 may be greater than 90 degrees relative to central axis 274. The axes 550, 552, 554, and 556 are defined by respective interfaces between each section and the flexible spine 320 (e.g., connection 312 of first section 210, connection 314 of second section 212, connection 316 of third section 214, and connection 318 of fourth section 216, respectively).

Each section may be angled by a different amount relative to one or more other sections in order to conform to the body of the patient. Further, although the angles 400, 402, and 404 are shown in the figures, each section is individually pivotable (e.g., rotatable and/or bendable) to a plurality of different angles within a range of angles (e.g., a range from 0 degrees to 180 degrees relative to the central axis 274), with the range of angles including the angles 400, 402, and 404. In each example, each of the sections may rotate by at least 90 degrees relative to the flexible spine 320 (e.g., relative to a respective interface of the sections with the flexible spine, such as connections 312, 314, 316, and 318). Further, the sections are flexible such that portions of each section may deform (e.g., bend) in different directions relative to other portions of each section (e.g., in order to wrap around the body of the patient).

The RF coil assembly 200 may increase SNR, fit a wider range of patients as if specially tailored to them, and allow for difficult scans to result in cleaner images. The RF coil assembly may also be lighter in weight than conventional RF coil assemblies, and may be easier to store when not in use.

Figure 7:
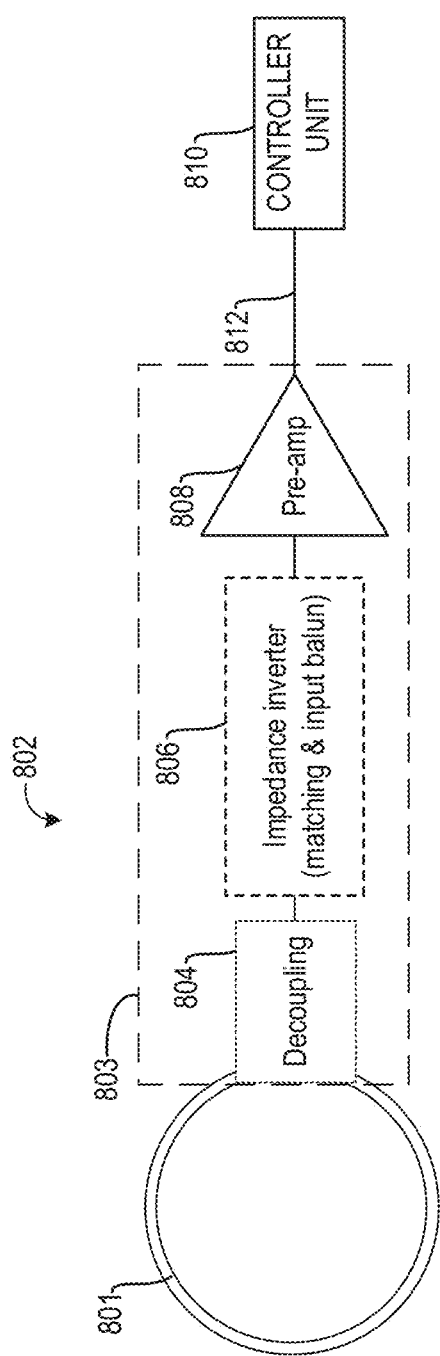
FIG. 7 schematically shows an example RF coil of an RF coil array coupled to a controller unit.

Turning now to FIG. 7, a schematic view of an RF coil 802 including a loop portion 801 coupled to a controller unit 810 via coupling electronics portion 803 and a coil-interfacing cable 812 is shown. In one example, the RF coil may be a surface receive coil, which may be single- or multi-channel. The RF coil 802 is one non-limiting example of RF coils included by RF coil unit 14 of FIG. 1 (e.g., similar to the RF coils included by RF coil assembly 200 described above) and as such may operate at one or more frequencies in the MRI apparatus 10 and the like. The coil-interfacing cable 812 may be a coil-interfacing cable extending between the electronics portion 803 and an interfacing connector of an RF coil (or an RF coil array). The coil-interfacing cable 812 may be an RF coil interfacing cable (or RF coil array interfacing cable) extending between the interfacing connector of the RF coil (or RF coil array) and the MRI system controller unit 810. The controller unit 810 may be associated with and/or may be a non-limiting example of the data processing unit 31 or controller unit 25 in FIG. 1.

The RF coil of the present disclosure includes a significantly smaller amount of copper, printed circuit board (PCB) material and electronic components than used in a conventional RF coil and includes paralleled elongated wire conductors, encapsulated and separated by a dielectric material, forming the coil element. The parallel wires form a low reactance structure without discrete capacitors. The minimal conductor, sized to keep losses tolerable, eliminates much of the capacitance between coil loops, and reduces electric field coupling. By interfacing with a large sampling impedance, currents are reduced and magnetic field coupling is minimized. The electronics are minimized in size and content to keep mass and weight low and prevent excessive interaction with the desired fields. Packaging can now be extremely flexible which allows contouring to anatomy, optimizing signal to noise ratio (SNR) and imaging acceleration.

A conventional RF receive coil for MR is comprised of several conductive intervals joined between themselves by capacitors. By adjusting the capacitors' values, the impedance of the RF coil may be brought to its minimal value, usually characterized by low resistance. At resonant frequency, stored magnetic and electric energy alternate periodically. Each conductive interval, due to its length and width, possesses a certain self-capacitance, where electric energy is periodically stored as static electricity. The distribution of this electricity takes place over the entire conductive interval length of the order of 5-15 cm, causing similar range electric dipole field. In a proximity of a large dielectric load, self-capacitance of the intervals change—hence detuning of the coil. In case of a lossy dielectric, dipole electric field causes Joule dissipation characterized by an increase overall resistance observed by the coil.

In contrast, the RF coil of the present disclosure represents almost an ideal magnetic dipole antenna as its common mode current is uniform in phase and amplitude along its perimeter. The capacitance of the RF coil is built between the two wires along the perimeter of the loop. The conservative electric field is strictly confined within the small cross-section of the two parallel wires and dielectric filler material. In the case of two RF coil loops overlapping, the parasitic capacitance at the cross-overs is greatly reduced in comparison to two overlapped copper traces of conventional RF coils. RF coil thin cross-sections allows increased magnetic decoupling and reduces or eliminates overlap between two loops in comparison to two conventional trace-based coil loops.

The coupling electronics portion 803 may be coupled to the loop portion of the RF coil 802. Herein, the coupling electronics portion 803 may include a decoupling circuit 804, impedance inverter circuit 806, and a pre-amplifier 808. The decoupling circuit 804 may effectively decouple the RF coil during a transmit operation. Typically, the RF coil 802 in its receive mode may be coupled to a body of a subject being imaged by the MR apparatus in order to receive echoes of the RF signal transmitted during the transmit mode. If the RF coil 802 is not used for transmission, RF coil 802 may be decoupled from the RF body coil while the RF body coil is transmitting the RF signal. The decoupling of the receive coil from the transmit coil may be achieved using resonance circuits and PIN diodes, microelectromechanical systems (MEMS) switches, or another type of switching circuitry. Herein, the switching circuitry may activate detuning circuits operatively connected to the RF coil 802.

The impedance inverter circuit 806 may form an impedance matching network between the RF coil 802 and the pre-amplifier 808. The impedance inverter circuit 806 is configured to transform a coil impedance of the RF coil 802 into an optimal source impedance for the pre-amplifier 808. The impedance inverter circuit 806 may include an impedance matching network and an input balun. The pre-amplifier 808 receives MR signals from the corresponding RF coil 802 and amplifies the received MR signals. In one example, the pre-amplifier may have a low input impedance that is configured to accommodate a relatively high blocking or source impedance. Additional details regarding the RF coil and associated coupling electronics portion will be explained in more detail below with respect to FIGS. 8 and 9. The coupling electronics portion 803 may be packaged in a very small PCB approximately 2 cm² in size or smaller. The PCB may be protected with a conformal coating or an encapsulating resin.

The coil-interfacing cable 812, such as an RF coil interfacing cable or RF coil array interfacing cable, may be used to transmit signals between the RF coils and other aspects of the processing system, for example to control the RF coils and/or to receive information from the RF coils. The RF coil interfacing cables or RF coil array interfacing cables may be disposed within the bore or imaging space of the MR apparatus (such as MRI apparatus 10 of FIG. 1) and subjected to electro-magnetic fields produced and used by the MRI apparatus. In MRI systems, coil-interfacing cables, such as coil-interfacing cable 812, may support transmitter-driven common-mode currents, which may in turn create field distortions and/or unpredictable heating of components. Typically, common-mode currents are blocked by using baluns. Baluns or common-mode traps provide high common-mode impedances, which in turn reduces the effect of transmitter-driven currents.

Thus, coil-interfacing cable 812 may include one or more baluns. In conventional coil-interfacing cables, baluns are positioned with a relatively high density, as high dissipation/voltages may develop if the balun density is too low or if baluns are positioned at an inappropriate location. However, this dense placement may adversely affect flexibility, cost, and performance. As such, the one or more baluns in the coil-interfacing cable may be continuous baluns to ensure no high currents or standing waves, independent of positioning. The continuous baluns may be distributed, flutter, and/or butterfly baluns. Additional details regarding the coil-interfacing cable and baluns will be presented below with respect to FIGS. 10-12.

Figure 8:
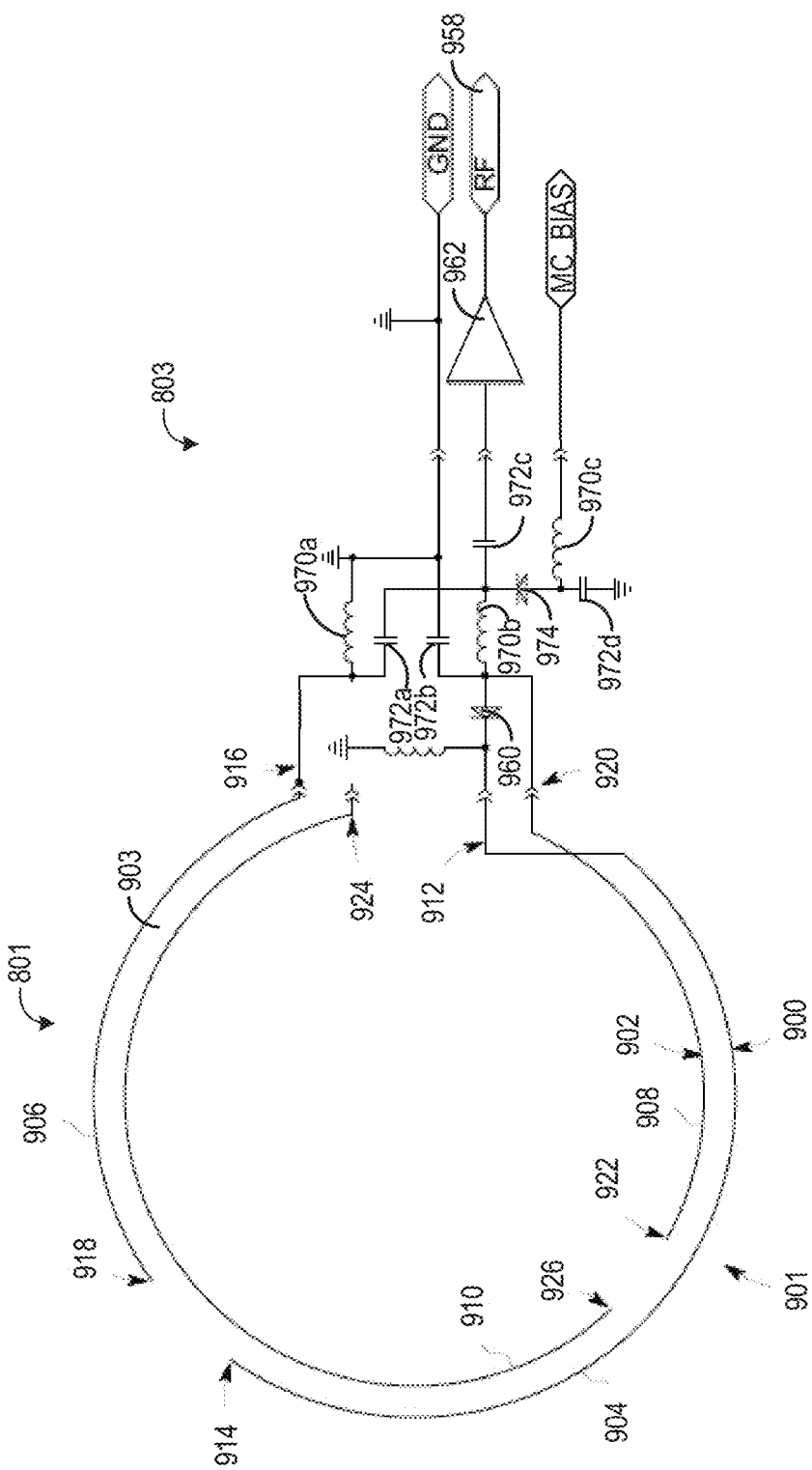
FIG. 8 shows a first example RF coil of an RF coil array and associated coupling electronics.

FIG. 8 is a schematic of an RF coil 901 having segmented conductors formed in accordance with an embodiment. RF coil 901 is a non-limiting example of RF coil 802 of FIG. 7 and as such includes loop portion 801 and coupling electronics portion 803 of RF coil 802. The coupling electronics portion allows the RF coil to transmit and/or receive RF signals when driven by the data acquisition unit 24 (shown in FIG. 1). In the illustrated embodiment, the RF coil 901 includes a first conductor 900 and a second conductor 902. The first and second conductors 900, 902 may be segmented such that the conductors form an open circuit (e.g., form a monopole). The segments of the conductors 900, 902 may have different lengths, as is discussed below. The length of the first and second conductors 900, 902 may be varied to achieve a select distributed capacitance, and accordingly, a select resonance frequency.

The first conductor 900 includes a first segment 904 and a second segment 906. The first segment 904 includes a driven end 912 at an interface terminating to coupling portion electronics 803, which will be described in more detail below. The first segment 904 also includes a floating end 914 that is detached from a reference ground, thereby maintaining a floating state. The second segment 906 includes a driven end 916 at the interface terminating to the coupling electronics portion and a floating end 918 that is detached from a reference ground.

The second conductor 902 includes a first segment 908 and a second segment 910. The first segment 908 includes a driven end 920 at the interface. The first segment 908 also includes a floating end 922 that is detached from a reference ground, thereby maintaining a floating state. The second segment 910 includes a driven end 924 at the interface, and a floating end 926 that is detached from a reference ground. The driven end 924 may terminate at the interface such that end 924 is only coupled to the first conductor through the distributed capacitance. The capacitors shown around the loop between the conductors represent the capacitance between the wires.

The first conductor 900 exhibits a distributed capacitance that grows based on the length of the first and second segments 904, 906. The second conductor 902 exhibits a distributed capacitance that grows based on the length of the first and second segments 908, 910. The first segments 904, 908 may have a different length than the second segments 906, 910. The relative difference in length between the first segments 904, 908 and the second segments 906, 910 may be used to produce an effective LC circuit have a resonance frequency at the desired center frequency. For example, by varying the length of the first segments 904, 908 relative to the lengths of the second segments 906, 910, an integrated distributed capacitance may be varied.

In the illustrated embodiment, the first and second conductors 900, 902 are shaped into a loop portion that terminates to an interface. But in other embodiments, other shapes are possible. For example, the loop portion may be a polygon, shaped to conform the contours of a surface (e.g., housing), and/or the like. The loop portion defines a conductive pathway along the first and second conductors. The first and second conductors are void of any discrete or lumped capacitive or inductive elements along an entire length of the conductive pathway. The loop portion may also include loops of varying gauge of stranded or solid conductor wire, loops of varying diameters with varying lengths of the first and second conductors 900, 902, and/or loops of varying spacing between the first and second conductors. For example, each of the first and second conductors may have no cuts or gaps (no segmented conductors) or one or more cuts or gaps (segmented conductors) at various locations along the conductive pathway.

Distributed capacitance (DCAP), as used herein, represents a capacitance exhibited between conductors that grows evenly and uniformly along the length of the conductors and is void of discrete or lumped capacitive components and discrete or lumped inductive components. In the examples herein, the capacitance may grow in a uniform manner along the length of the first and second conductors 900, 902.

A dielectric material 903 encapsulates and separates the first and second conductors 900, 902. The dielectric material 903 may be selectively chosen to achieve a select distributive capacitance. The dielectric material 903 may be based on a desired permittivity $\in$ to vary the effective capacitance of the loop portion. For example, the dielectric material 903 may be air, rubber, plastic, or any other dielectric material. In one example, the dielectric material may be polytetrafluoroethylene (pTFE). For example, the dielectric material 903 may be an insulating material surrounding the parallel conductive elements of the first and second conductors 900, 902. Alternatively, the first and second conductors 900, 902 may be twisted upon one another to form a twisted pair cable. As another example, the dielectric material 903 may be a plastic material. The first and second conductors 900, 902 may form a coaxial structure in which the plastic dielectric material 903 separates the first and second conductors. As another example, the first and second conductors may be configured as planar strips.

The coupling electronics 803 is operably and communicatively coupled to the RF driver unit 22, the data acquisition unit 24, controller unit 25, and/or data processing unit 31 to allow the RF coil 802 to transmit and/or receive RF signals. In the illustrated embodiment, the coupling electronics 803 includes a signal interface 958 configured to transmit and receive the RF signals.

As explained above with reference to FIG. 7, the coupling electronics 803 includes a decoupling circuit, impedance inverter circuit, and pre-amplifier. As illustrated in FIG. 8, the decoupling circuit includes a decoupling diode 960. The decoupling diode 960 may be provided with voltage from MC_BIAS, for example, in order to turn decoupling diode 960 on. When on, decoupling diode 960 causes conductor 900 to short with conductor 902, thus causing the coil be off-resonance and hence decouple the coil during a transmit operation, for example.

The impedance inverter circuit includes a plurality of inductors, including first inductor 970a, second inductor 970b, and third inductor 970c; a plurality of capacitors, including first capacitor 972a, a second capacitor 972b, a third capacitor 972c, and a fourth capacitor 972d; and a diode 974. The impedance inverter circuit includes matching circuitry and an input balun. As shown, the input balun is a lattice balun that comprises first inductor 970a, second inductor 970b, first capacitor 972a, and second capacitor 972b. In one example, diode 974 limits the direction of current flow to block RF receive signals from proceeding into decoupling bias branch (MC_BIAS).

In one example, the RF, GND, and MC_BIAS connections are part of a single cable. For example, the cable may be a triaxial cable with a center conductor and two surrounding shields. The center conductor may electrically conduct the RF signal and pre-amp control, a first shield may be the GND connection (e.g., ground), and a second, outermost shield may be the MC_BIAS connection (e.g., multi-coil bias for diode decoupling control). The cable may connect to an interface board (along with one or more other cables of RF coils), with a connector of the interface board electrically coupling the cable to the MRI system.

The pre-amplifier 962 may be a low input impedance pre-amplifier that is optimized for high source impedance by the impedance matching circuitry. The pre-amplifier may have a low noise reflection coefficient, $\gamma$, and a low noise resistance, Rn. In one example, the pre-amplifier may have a source reflection coefficient of $\gamma$ substantially equal to 0.0 and a normalized noise resistance of Rn substantially equal to 0.0 in addition to the low noise figure. However, $\gamma$ values substantially equal to or less than 0.1 and Rn values substantially equal to or less than 0.2 are also contemplated. With the pre-amplifier having the appropriate $\gamma$ and Rn values, the pre-amplifier provides a blocking impedance for RF coil 901 while also providing a large noise circle in the context of a Smith Chart. As such, current in RF coil 901 is minimized, the pre-amplifier is effectively noise matched with RF coil 901 output impedance. Having a large noise circle, the pre-amplifier yields an effective SNR over a variety of RF coil impedances while producing a high blocking impedance to RF coil 901.

In some examples, the pre-amplifier 962 may include an impedance transformer that includes a capacitor and an inductor. The impedance transformer may be configured to alter the impedance of the pre-amplifier to effectively cancel out a reactance of the pre-amplifier, such as capacitance caused by a parasitic capacitance effect. Parasitic capacitance effects can be caused by, for example, a PCB layout of the pre-amplifier or by a gate of the pre-amplifier. Further, such reactance can often increase as the frequency increases. Advantageously, however, configuring the impedance transformer of the pre-amplifier to cancel, or at least minimize, reactance maintains a high impedance (e.g., a blocking impedance) to RF coil 901 and an effective SNR without having a substantial impact on the noise figure of the pre-amplifier. The lattice balun described above may be a non-limiting example of an impedance transformer.

In examples, the pre-amplifier described herein may a low input pre-amplifier. For example, in some embodiments, a "relatively low" input impedance of the preamplifier is less than approximately 5 ohms at resonance frequency. The coil impedance of the RF coil 901 may have any value, which may be dependent on coil loading, coil size, field strength, and/or the like. Examples of the coil impedance of the RF coil 901 include, but are not limited to, between approximately 2 ohms and approximately 10 ohms at 1.5 T magnetic field strength, and/or the like. The impedance inverter circuitry is configured to transform the coil impedance of the RF coil 901 into a relatively high source impedance. For example, in some embodiments, a "relatively high" source impedance is at least approximately 100 ohms and may be greater than 150 ohms.

The impedance transformer may also provide a blocking impedance to the RF coil 901. Transformation of the coil impedance of the RF coil 901 to a relative high source impedance may enable the impedance transformer to provide a higher blocking impedance to the RF coil 901. Exemplary values for such higher blocking impedances include, for example, a blocking impedance of at least 500 ohms, and at least 1000 ohms.

Figure 9:
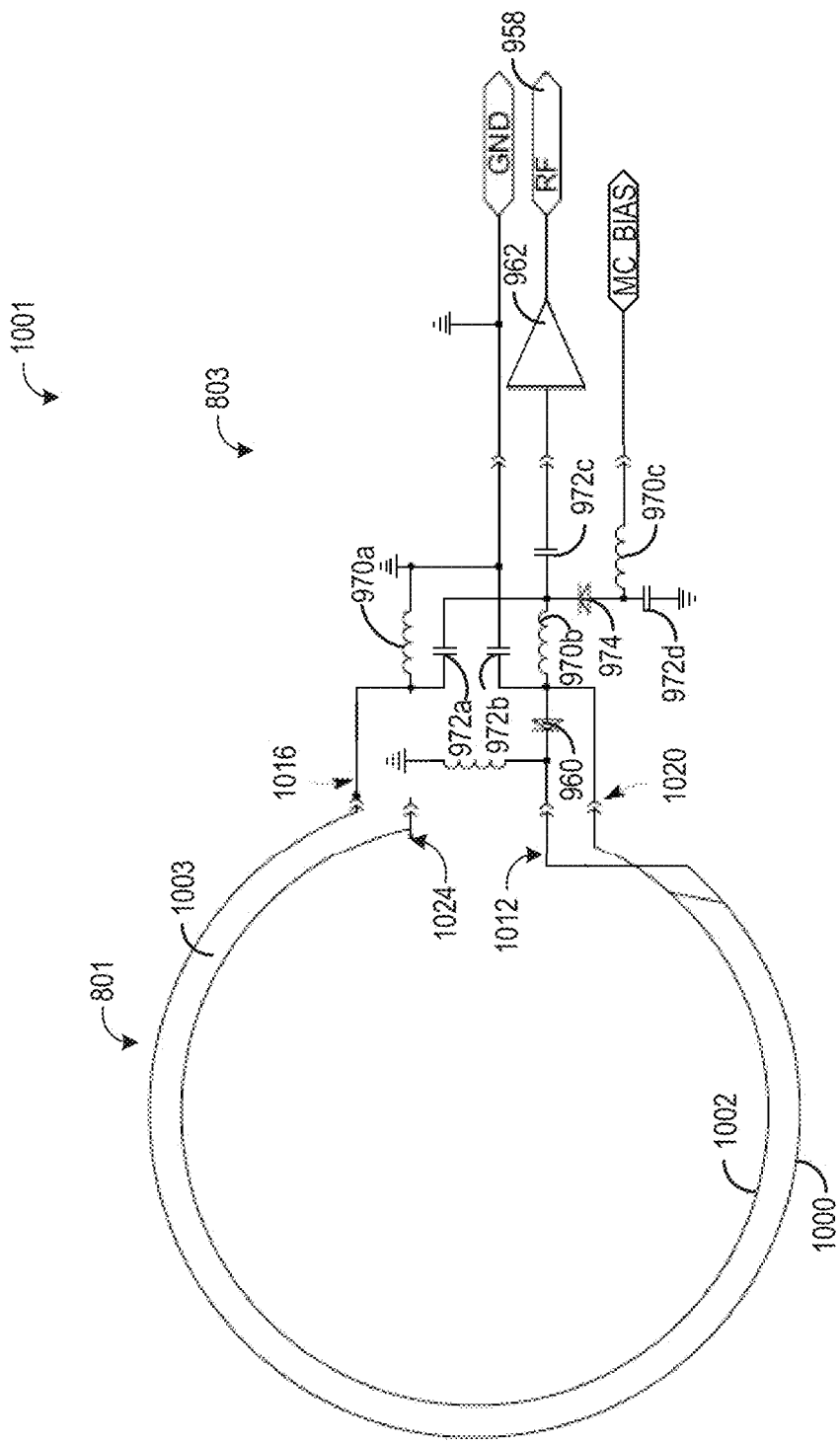
FIG. 9 shows a second example RF coil of an RF coil array and associated coupling electronics.
Figure 10:
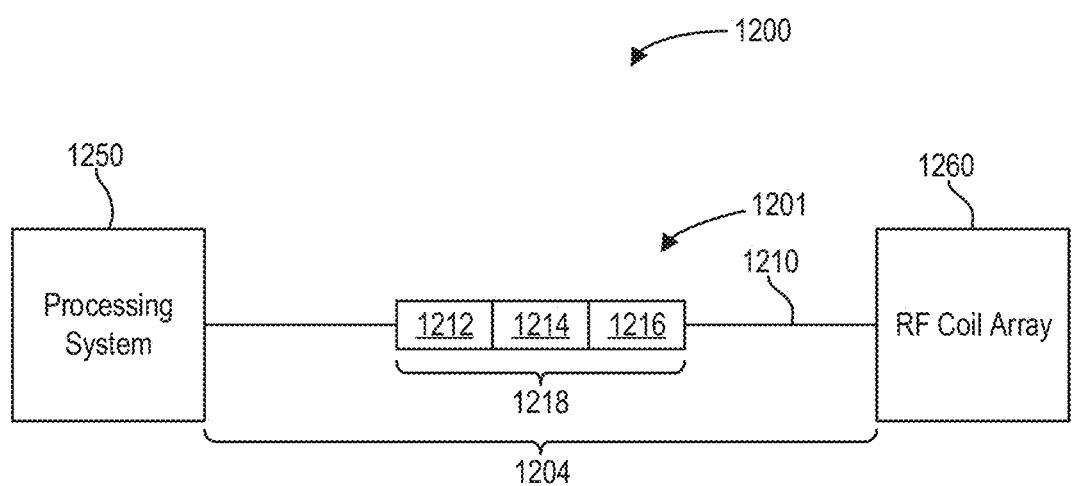
FIG. 10 schematically shows an example RF coil array interfacing cable including a plurality of continuous and/or contiguous common mode traps positioned between a processing system and an RF coil array of a MRI system.

FIG. 9 is a schematic of an RF coil 1001 and coupling electronics 803 according to another embodiment. The RF coil of FIG. 10 is a non-limiting example of the RF coil and coupling electronics of FIG. 7, and as such includes a loop portion 801 and coupling electronics portion 803. The coupling electronics allows the RF coil to transmit and/or receive RF signals when driven by the data acquisition unit 24 (shown in FIG. 1). The RF coil 1001 includes a first conductor 1000 in parallel with a second conductor 1002. At least one of the first and second conductors 1000, 1002 are elongated and continuous.

In the illustrated embodiment, the first and second conductors 1000, 1002 are shaped into a loop portion that terminates to an interface. But in other embodiments, other shapes are possible. For example, the loop portion may be a polygon, shaped to conform the contours of a surface (e.g., housing), and/or the like. The loop portion defines a conductive pathway along the first and second conductors 1000, 1002. The first and second conductors 1000, 1002 are void of any discrete or lumped capacitive or inductive components along an entire length of the conductive pathway. The first and second conductors 1000, 1002 are uninterrupted and continuous along an entire length of the loop portion. The loop portion may also include loops of varying gauge of stranded or solid conductor wire, loops of varying diameters with varying lengths of the first and second conductors 1000, 1002, and/or loops of varying spacing between the first and second conductors. For example, each of the first and second conductors may have no cuts or gaps (no segmented conductors) or one or more cuts or gaps (segmented conductors) at various locations along the conductive pathway.

The first and second conductors 1000, 1002 have a distributed capacitance along the length of the loop portion (e.g., along the length of the first and second conductors 1000, 1002). The first and second conductors 1000, 1002 exhibit a substantially equal and uniform capacitance along the entire length of the loop portion. Distributed capacitance (DCAP), as used herein, represents a capacitance exhibited between conductors that grows evenly and uniformly along the length of the conductors and is void of discrete or lumped capacitive components and discrete or lumped inductive components. In the examples herein, the capacitance may grow in a uniform manner along the length of the first and second conductors 1000, 1002. At least one of the first and second conductors 1000, 1002 are elongated and continuous. In the illustrated embodiment, both the first and second conductors 1000, 1002 are elongated and continuous. But in other embodiments, only one of the first or second conductors 1000, 1002 may be elongated and continuous. The first and second conductors 1000, 1002 form continuous distributed capacitors. The capacitance grows at a substantially constant rate along the length of the conductors 1000, 1002. In the illustrated embodiment, the first and second conductors 1000, 1002 forms an elongated continuous conductors that exhibits DCAP along the length of the first and second conductors 1000, 1002. The first and second conductors 1000, 1002 are void of any discrete capacitive and inductive components along the entire length of the continuous conductors between terminating ends of the first and second conductors 1000, 1002. For example, the first and second conductors 1000, 1002 does not include any discrete capacitors, nor any inductors along the length of the loop portion.

A dielectric material 1003 separates the first and second conductors 1000, 1002. The dielectric material 1003 may be selectively chosen to achieve a select distributive capacitance. The dielectric material 1003 may be based on a desired permittivity $\in$ to vary the effective capacitance of the loop portion. For example, the dielectric material 1003 may be air, rubber, plastic, or any other dielectric material. In one example, the dielectric material may be polytetrafluoroethylene (pTFE). For example, the dielectric material 1003 may be an insulating material surrounding the parallel conductive elements of the first and second conductors 1000, 1002. Alternatively, the first and second conductors 1000, 1002 may be twisted upon one another to from a twisted pair cable. As another example, the dielectric material 1003 may be a plastic material. The first and second conductors 1000, 1002 may form a coaxial structure in which the plastic dielectric material 1003 separates the first and second conductors 1000, 1002. As another example, the first and second conductors 1000, 1002 may be configured as planar strips.

The first conductor 1000 includes a first terminating end 1012 and a second terminating end 1016 that terminates at the interface. The first terminating end 1012 is coupled to the coupling electronics 803. The first terminating end 1012 may also be referred to herein as a "drive end." The second terminating end 1016 is also referred to herein as a "second drive end."

The second conductor 1002 includes a first terminating end 1020 and a second terminating end 1024 that terminates at the interface. The first terminating end 1020 is coupled to the coupling electronics 803. The first terminating end 1020 may also be referred to herein as a "drive end." The second terminating end 1024 is also referred to herein as a "second drive end."

The loop portion 801 of the RF coil 1001 is coupled to coupling electronics 803. The coupling electronics 803 may be the same coupling electronics described above with respect to FIGS. 7 and 8, and hence like reference numbers are given to like components and further description is dispensed with.

As appreciated by FIGS. 8 and 9, the two parallel conductors comprising the loop portion of an RF coil may each be continuous conductors, as illustrated in FIG. 9, or one or both of the conductors may be non-continuous, as illustrated in FIG. 8. For example, both conductors shown in FIG. 8 may include cuts, resulting in each conductor being comprised of two segments. The resulting space between conductor segments may be filled with the dielectric material that encapsulates and surrounds the conductors. The two cuts may be positioned at different locations, e.g., one cut at 1350 and the other cut at 2250 (relative to where the loop portion interfaces with the coupling electronics). By including discontinuous conductors, the resonance frequency of the coil may be adjusted relative to a coil that includes continuous conductors. In an example, an RF coil that includes two continuous parallel conductors encapsulated and separated by a dielectric, the resonance frequency may be a smaller, first resonance frequency. If that RF coil instead includes one discontinuous conductor (e.g., where one of the conductors is cut and filled with the dielectric material) and one continuous conductor, with all other parameters (e.g., conductor wire gauge, loop diameter, spacing between conductors, dielectric material) being the same, the resonance frequency of the RF coil may be a larger, second resonance frequency. In this way, parameters of the loop portion, including wire gauge, loop diameter, spacing between wire conductors, dielectric material selection and/or thickness, and conductor segment number and lengths, may be adjusted to tune the RF coil to a desired resonance frequency.

The RF coils presented above with respect to FIGS. 7-9 may be utilized in order to receive MR signals during an MR imaging session. As such, the RF coils of FIGS. 7-9 may be non-limiting examples of RF coils included by RF coil unit 14 of FIG. 1 (and may be similar to RF coils included by RF coil assembly 200, described above) and may be configured to be coupled to a downstream component of the MRI system, such as a processing system. The RF coils of FIGS. 7-9 may be present as single RF coils (e.g., as a single, only RF coil of one of sections 210, 212, 214, or 216 described above) or in an array of RF coils having various configurations. Various configurations of RF coils and accompanying coil-interfacing cables similar to the RF coils described above with respect to FIGS. 7-9 may be possible, as described below.

An RF coil array including RF coils similar to those described above may include a coil loop and an electronics unit coupled to each coil, and a coil-interfacing cable connected to and extending from each coupling electronics unit. Accordingly, the RF coil array may include (for example) four coil loops, four electronics units, and four coil-interfacing cables. A different, second RF coil array may include a separate electronics unit for each coil loop, with each electronics unit coupled to a respective coil-interfacing cable. The second RF coil array may include four coil loops, four electronics units, and four coil-interfacing cables (for example) that are bundled together in a single grouping of four coil-interfacing cables, and may be referred to as an integrated balun cable harness. Each coil-interfacing cable coupled to a respective electronics unit may combine into one overall coil-interfacing cable, also referred to as a cable assembly.

The individual coupling electronics units may be housed in a common electronics housing in some examples. Each coil loop (e.g., of the coil array) may have respective coupling electronics unit (e.g., a decoupling circuit, impedance inverter circuit, and pre-amplifier) housed in the housing. In some examples, the common electronics housing may be detachable from the coil loop or RF coil array. In one example, the electronics may be placed in a separable assembly and disconnected from the RF coil array. A connector interface could be placed at, for example, the junctions between the conductor loop portions (e.g., the drive ends described above) and the coupling electronics for each individual coupling electronics unit.

The wire conductors and coil loops used in the RF coils or RF coil arrays described herein may be manufactured in any suitable manner to get the desired resonance frequency for a desired RF coil application. The desired wire gauge, such as 28 or 30 American Wire Gauge (AWG) or any other desired wire gauge may be paired with a parallel wire of the same gauge and encapsulated with a dielectric material using an extrusion process or a three-dimensional (3D) printing or additive manufacturing process. This manufacturing process may be environmentally friendly with low waste and low-cost.

Thus, the RF coils described herein includes a twin lead wire conductor loop encapsulated in a pTFE dielectric that may have no cuts or with at least one cut in at least one of the two parallel wire conductors and a miniaturized coupling electronics PCB coupled to each coil loop (e.g., very small coupling electronics PCB approximately the sizer of 2 cm$^2$ or smaller). The PCBs may be protected with a conformal coating or an encapsulation resin. In doing so, conventional components are eliminated and capacitance is "built in" the integrated capacitor (INCA) coil loops. Interactions between coil elements are reduced or eliminated. The coil loops are adaptable to a broad range of MR operating frequencies by changing the gauge of wire used, spacing between wires, loop diameters, loop shapes, and the number and placement of cuts in the wires.

The coil loops are transparent in PET/MR applications, aiding dose management and signal-to-noise ratios (SNR). The miniaturized coupling electronics PCB includes decoupling circuitry, impedance inverter circuitry with impedance matching circuitry and an input balun, and a pre-amplifier. The pre-amplifier sets new standards in coil array applications for lowest noise, robustness, and transparency. The pre-amplifier provides active noise cancelling to reduce current noise, boost linearity, and increase tolerance to varying coil loading conditions. Additionally, as explained in more detail below, a cable harness with baluns for coupling each of the miniaturized coupling electronics PCBs to the RF coil array connector that interfaces with the MRI system may be provided.

The RF coils described herein are exceptionally lightweight, and may weigh less than 10 grams per coil element versus 45 grams per coil element with General Electric Company's Geometry Embracing Method (GEM) suite of flexible RF coil arrays. For example, a 16-channel RF coil array according to the disclosure may weigh less than 0.5 kg. The RF coils described herein are exceptionally flexible and durable as the coils are extremely simple with very few rigid components to damage and allowing floating overlaps. The RF coils described herein are exceptionally low cost (e.g., greater than a ten times reduction from conventional RF coils). For example, a 16-channel RF coil array could be comprised of components and materials of less than $50. The RF coils described herein do not preclude current packaging or emerging technologies and could be implemented in RF coil arrays that are not packaged or attached to a former, or implemented in RF coil arrays that are attached to flexible formers as flexible RF coil arrays or attached to rigid formers as rigid RF coil arrays.

The combination of an INCA coil loop and associated coupling electronics is a single coil element, which is functionally independent and electrically immune to its surrounding environment or neighboring coil elements. As a result, the RF coils described herein perform equally well in low and high-density coil array applications. The exceptional isolation between coil elements allows the overlap between coil elements to be maximized without degrading performance across coil elements. This allows for a higher density of coil elements than is possible with conventional RF coil array designs.

In some examples, the RF coils included by RF coil assembly 200 (as described above) may be positioned in a different relative arrangement than those shown by FIGS. 2-6. For example, the RF coils included by RF coil assembly 200 may be electrically coupled together as one or more sets (e.g., sub-arrays) of RF coils, and the one or more sets may include the RF coils positioned in various different arrangements relative to those shown by FIGS. 2-6.

FIG. 10 illustrates a block schematic diagram of a continuous common mode trap assembly 1200 formed in accordance with various embodiments. The common mode trap assembly 1200 may be configured as a transmission cable 1201 configured for transmission of signals between a processing system 1250 and an RF coil or RF coil array of an MRI system (e.g., the RF coils of RF coil assembly 200, such as RF coils of the first coil array 202, second coil array 204, etc.). Transmission cable 1201 is a non-limiting example of RF coil array interfacing cable 812, processing system 1250 is a non-limiting example of controller unit 810, and RF coil array 1260 is a non-limiting example of a plurality of RF coils 802 and coupling electronics 803 of FIG. 7.

In the illustrated embodiment, the transmission cable 1201 (or RF coil array interfacing cable) includes a central conductor 1210 and plural common mode traps 1212, 1214, 1216. It may be noted that, while the common mode traps 1212, 1214, and 1216 are depicted as distinct from the central conductor 1210, in some embodiments, the common mode traps 1212, 1214, 1216 may be integrally formed with or as a part of the central conductor 1210.

The central conductor 1210 in the illustrated embodiment has a length 1204, and is configured to transmit a signal between the RF coil array 1260 and at least one processor of an MRI system (e.g., processing system 1250). The central conductor 1210 may include one or more of a ribbon conductor, a wire, or a coaxial cable bundle, for example. The length 1204 of the depicted central conductor 1210 extends from a first end of the central conductor 1210 (which is coupled to the processing system 1250) to a second end of the central conductor 1210 (which is coupled to the RF coil array 1260). In some embodiments, the central conductor may pass through a central opening of the common mode traps 1212, 1214, 1216.

The depicted common mode traps 1212, 1214, 1216 (which may be understood as cooperating to form a common mode trap unit 1218), as seen in FIG. 10, extend along at least a portion of the length 1204 of the central conductor 1210. In the illustrated embodiment, common mode traps 1212, 1214, 1216 do not extend along the entire length 1204. However, in other embodiments, the common mode traps 1212, 1214, 1216 may extend along the entire length 1204, or substantially along the entire length 1204 (e.g., along the entire length 1204 except for portions at the end configured to couple, for example, to a processor or RF coil array). The common mode traps 1212, 1214, 1216 are disposed contiguously. As seen in FIG. 10, each of the common mode traps 1212, 1214, 1216 is disposed contiguously to at least one other of the common mode traps 1212, 1214, 1216. As used herein, contiguous may be understood as including components or aspects that are immediately next to or in contact with each other. For example, contiguous components may be abutting one another. It may be noted that in practice, small or insubstantial gaps may be between contiguous components in some embodiments. In some embodiments, an insubstantial gap (or conductor length) may be understood as being less than ¹⁄₄₀th of a wavelength of a transmit frequency in free space. In some embodiments, an insubstantial gap (or conductor length) may be understood as being two centimeters or less. Contiguous common mode traps, for example, have no (or insubstantial) intervening gaps or conductors therebetween that may be susceptible to induction of current from a magnetic field without mitigation provided by a common mode trap.

For example, as depicted in FIG. 10, the common mode trap 1212 is contiguous to the common mode trap 1214, the common mode trap 1214 is contiguous to the common mode trap 1212 and the common mode trap 1216 (and is interposed between the common mode trap 1212 and the common mode trap 1216), and the common mode trap 1216 is contiguous to the common mode trap 1214. Each of the common mode traps 1212, 1214, 1216 are configured to provide an impedance to the receive transmitter driven currents of an MRI system. The common mode traps 1212, 1214, 1216 in various embodiments provide high common mode impedances. Each common mode trap 1212, 1214, 1216, for example, may include a resonant circuit and/or one or more resonant components to provide a desired impedance at or near a desired frequency or within a target frequency range. It may be noted that the common mode traps 1212, 1214, 1216 and/or common mode trap unit 1218 may also be referred to as chokes or baluns by those skilled in the art.

In contrast to systems having separated discrete common mode traps with spaces therebetween, various embodiments (e.g., the common mode trap assembly 1200) have a portion over which common mode traps extend continuously and/or contiguously, so that there are no locations along the portion for which a common mode trap is not provided. Accordingly, difficulties in selecting or achieving particular placement locations of common mode traps may be reduced or eliminated, as all locations of interest may be included within the continuous and/or contiguous common mode trap. In various embodiments, a continuous trap portion (e.g., common mode trap unit 1218) may extend along a length or portion thereof of a transmission cable.

The continuous mode trap portion may be formed of contiguously-joined individual common mode traps or trap sections (e.g., common mode traps 1212, 1214, 1216). Further, contiguous common mode traps may be employed in various embodiments to at least one of lower the interaction with coil elements, distribute heat over a larger area (e.g., to prevent hot spots), or help ensure that blocking is located at desired or required positions. Further, contiguous common mode traps may be employed in various embodiments to help distribute voltage over a larger area. Additionally, continuous and/or contiguous common mode traps in various embodiments provide flexibility. For example, in some embodiments, common mode traps may be formed using a continuous length of conductor(s) (e.g., outer conductors wrapped about a central conductor) or otherwise organized as integrally formed contiguous sections. In various embodiments, the use of contiguous and/or continuous common mode traps (e.g., formed in a cylinder) provide for a range of flexibility over which flexing of the assembly does not substantially change the resonant frequency of the structure, or over which the assembly remains on frequency as it is flexed.

It may be noted that the individual common mode traps or sections (e.g., common mode traps 1212, 1214, 1216) in various embodiments may be constructed or formed generally similarly to each other (e.g., each trap may be a section of a length of tapered wound coils), but each individual trap or section may be configured slightly differently than other traps or sections. For example, in some embodiments, each common mode trap 1212, 1214, 1216 is tuned independently. Accordingly, each common mode trap 1212, 1214, 1216 may have a resonant frequency that differs from other common mode traps of the same common mode trap assembly 1200.

Alternatively or additionally, each common mode trap may be tuned to have a resonant frequency near an operating frequency of the MRI system. As used herein, a common mode trap may be understood as having a resonant frequency near an operating frequency when the resonant frequency defines or corresponds to a band that includes the operating frequency, or when the resonant frequency is close enough to the operating frequency to provide on-frequency blocking, or to provide a blocking impedance at the operating frequency.

Further additionally or alternatively, each common mode trap may be tuned to have a resonant frequency below an operating frequency of the MRI system (or each common mode trap may be tuned to have resonant frequency above an operating frequency of the MRI system). With each trap having a frequency below (or alternatively, with each trap having a frequency above) the operating frequency, the risk of any of the traps canceling each other out (e.g., due to one trap having a frequency above the operating frequency and a different trap having a frequency below the operating frequency) may be eliminated or reduced. As another example, each common mode trap may be tuned to a particular band to provide a broadband common mode trap assembly.

In various embodiments, the common mode traps may have a two-dimensional (2D) or three-dimensional (3D) butterfly configuration to counteract magnetic field coupling and/or local distortions.

Figure 11:
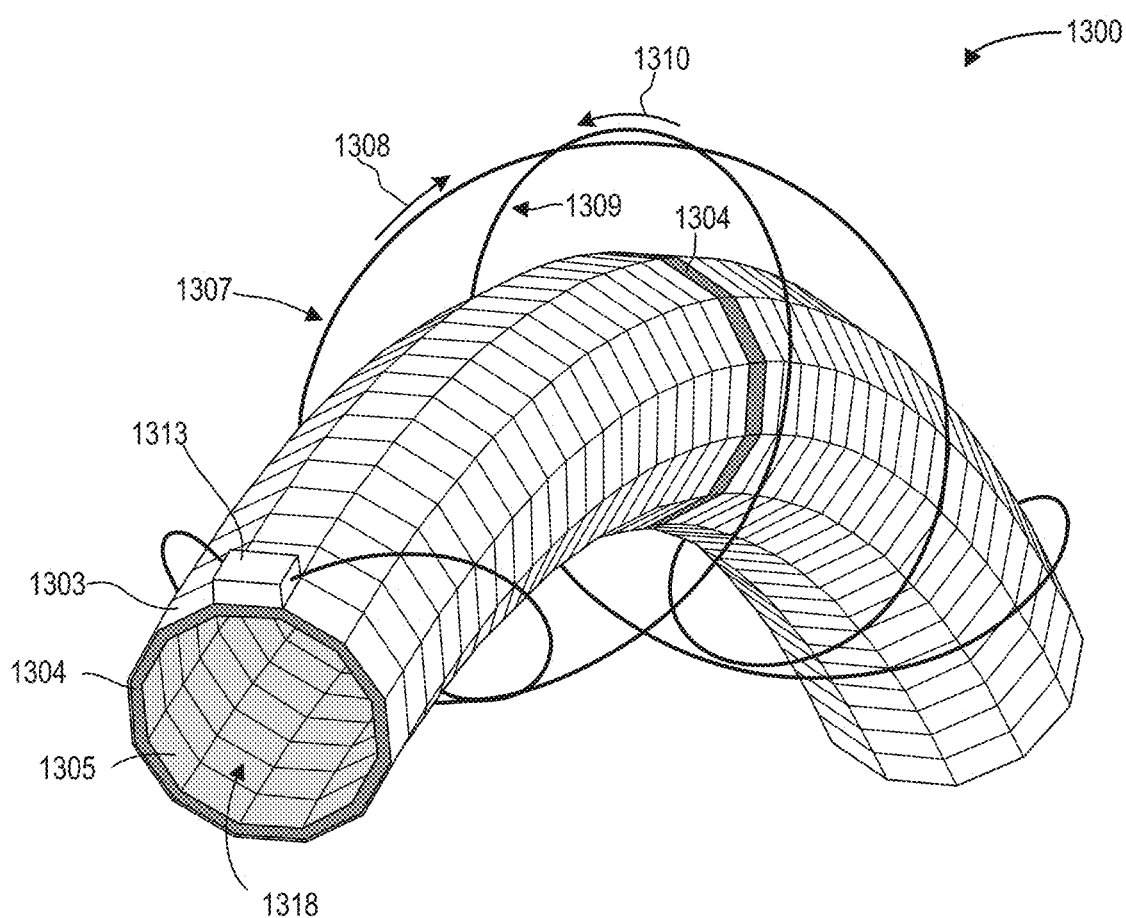
FIGS. 11 and 12 schematically show example RF coil array interfacing cables including a plurality of continuous and/or contiguous common mode traps.

FIG. 11 is a perspective view of an RF coil array interfacing cable 1300 including a plurality of continuous and/or contiguous common mode traps according to an embodiment of the disclosure. The RF coil array interfacing cable 1300 includes an outer sleeve or shield 1303, a dielectric spacer 1304, an inner sleeve 1305, a first common mode trap conductor 1307, and a second common mode trap conductor 1309.

The first common mode trap conductor 1307 is wrapped in a spiral about the dielectric spacer 1304, or wrapped in a spiral at a tapering distance from a central conductor (not shown) disposed within the bore 1318 of the RF coil array interfacing cable 1300, in a first direction 1308. Further, the second common mode trap conductor 1309 is wrapped in a spiral about the dielectric spacer 1304, or wrapped in a spiral at a tapering distance from the central conductor disposed within the bore 1318, in a second direction 1310 that is opposite to the first direction 1308. In the illustrated embodiment, the first direction 1308 is clockwise and the second direction 1310 is counter-clockwise.

The conductors 1307 and 1309 of the RF coil array interfacing cable 1300 may comprise electrically-conductive material (e.g., metal) and may be shaped as ribbons, wires, and/or cables, for example. In some embodiments, the counterwound or outer conductors 1307 and 1309 may serve as a return path for a current passing through the central conductor. Further, in various embodiments, the counterwound conductors 1307 and 1309 may cross each other orthogonally (e.g., a center line or path defined by the first common mode trap conductor 1307 is perpendicular to a center line or path defined by the second common mode trap conductor 1309 as the common mode trap conductors cross paths) to eliminate, minimize, or reduce coupling between the common mode trap conductors.

It may be further noted that in various embodiments the first common mode trap conductor 1307 and the second common mode trap conductor 1309 are loosely wrapped about the dielectric spacer 1304 to provide flexibility and/or to reduce any binding, coupling, or variation in inductance when the RF coil array interfacing cable 1300 is bent or flexed. It may be noted that the looseness or tightness of the counterwound outer conductors may vary by application (e.g., based on the relative sizes of the conductors and dielectric spacer, the amount of bending or flexing that is desired for the common mode trap, or the like). Generally, the outer or counterwound conductors may be tight enough so that they remain in the same general orientation about the dielectric spacer 1304, but loose enough to allow a sufficient amount of slack or movement during bending or flexing of the RF coil array interfacing cable 1300 to avoid, minimize, or reduce coupling or binding of the counterwound outer conductors.

In the illustrated embodiment, the outer shielding 1303 is discontinuous in the middle of the RF coil array interfacing cable 1300 to expose a portion of the dielectric spacer 1304 which in some embodiments is provided along the entire length of the RF coil array interfacing cable 1300. The dielectric spacer 1304, may be comprised, as a non-limiting example, of Teflon or another dielectric material. The dielectric spacer 1304 functions as a capacitor and thus may be tuned or configured to provide a desired resonance. It should be appreciated that other configurations for providing capacitance to the RF coil array interfacing cable 1300 are possible, and that the illustrated configurations are exemplary and non-limiting. For example, discrete capacitors may alternatively be provided to the RF coil array interfacing cable 1300.

Further, the RF coil array interfacing cable 1300 includes a first post 1313 and a second post (not shown) to which the first common mode trap conductor 1307 and the second common mode trap conductor 1309 are fixed. To that end, the first post 1313 and the second post are positioned at the opposite ends of the common mode trap, and are fixed to the outer shielding 1303. The first post 1313 and the second post ensure that the first and second common mode trap conductors 1307 and 1309 are positioned close to the outer shielding 1303 at the ends of the RF coil array interfacing cable 1300, thereby providing a tapered butterfly configuration of the counterwound conductors as described further herein.

The tapered butterfly configuration includes a first loop formed by the first common mode trap conductor 1307 and a second loop formed by the second common mode trap conductor 1309, arranged so that an induced current (a current induced due to a magnetic field) in the first loop 1307 and an induced current in the second loop 1309 cancel each other out. For example, if the field is uniform and the first loop 1307 and the second loop 1309 have equal areas, the resulting net current will be zero. The tapered cylindrical arrangement of the loops 1307 and 1309 provide increased flexibility and consistency of resonant frequency during flexing relative to two-dimensional arrangements conventionally used in common mode traps.

Generally, a tapered butterfly configuration as used herein may be used to refer to a conductor configuration that is flux cancelling, for example including at least two similarly sized opposed loops that are symmetrically disposed about at least one axis and are arranged such that currents induced in each loop (or group of loops) by a magnetic field tends to cancel out currents induced in at least one other loop (or group of loops). For example, with reference to FIG. 10, in some embodiments, counterwound conductors (e.g., conductors wound about a central member and/or axis in opposing spiral directions) may be spaced a distance radially from the central conductor 1210 to form the common mode traps 1212, 1214, 1216. As depicted in FIG. 11, the radial distance may be tapered towards the end of the common mode traps to reduce or altogether eliminate fringe effects. In this way, the common mode traps 1212, 1214, 1216 may be continuously or contiguously positioned without substantial gaps therebetween.

Figure 12:
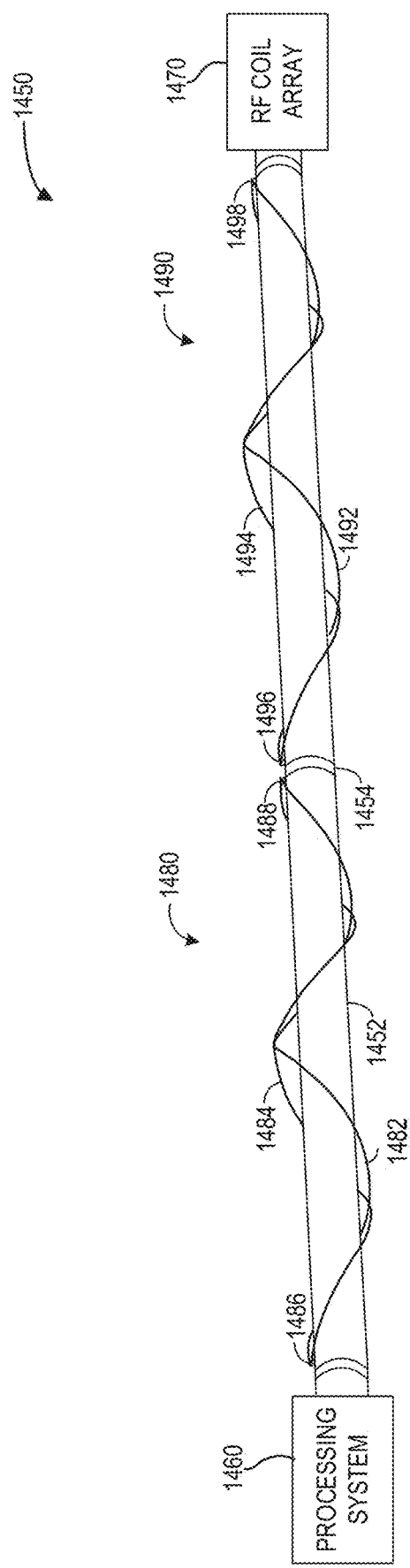

The tapered spiral configuration of the common mode trap conductors described herein above is particularly advantageous when multiple common mode trap conductors are contiguously disposed in a common mode trap assembly. As an illustrative example, FIG. 12 is a perspective view of an RF coil array interfacing cable 1450 including a plurality of continuous and/or contiguous common mode traps coupling an RF coil 1470 to a processing system 1460. RF coil array interfacing cable 1450 includes a first common mode trap 1480 and a second common mode trap 1490 positioned adjacent to each other on a central conductor 1452.

The first common mode trap 1480 includes a first common mode trap conductor 1482 and a second common mode trap conductor 1484 counterwound in a tapered spiral configuration. To that end, the first and second conductors 1482 and 1484 are fixed to posts 1486 and 1488. It should be noted that the posts 1486 and 1488 are aligned on a same side of the common mode trap 1480.

Similarly, the second common mode trap 1490 includes a third common mode trap conductor 1492 and a fourth common mode trap conductor 1494 counterwound in a tapered spiral configuration and fixed to posts 1496 and 1498. It should be noted that the posts 1496 and 1498 are aligned on a same side of the common mode trap 1490.

As depicted, the common mode traps 1480 and 1490 are separated by a distance, thereby exposing the central conductor 1452 in the gap 1454 between the common mode traps. Due to the tapering spiral configuration of the common mode trap conductors of the common mode traps, the gap 1454 can be minimized or altogether eliminated in order to increase the density of common mode traps in a common mode trap assembly without loss of impedance functions of the common mode traps. That is, the distance can be made arbitrarily small such that the common mode traps are in contact, given the tapered spiral configuration.

It should be appreciated that while the RF coil array interfacing cable 1450 includes two common mode traps 1480 and 1490, in practice an RF coil array interfacing cable may include more than two common mode traps.

Further, the common mode traps 1480 and 1490 of the RF coil array interfacing cable 1450 are aligned such that the posts 1486, 1488, 1496, and 1498 are aligned on a same side of the RF coil array interfacing cable. However, in examples where cross-talk between the common mode traps may be possible, for example if the tapering of the counterwound conductors is more severe or steep, the common mode traps may be rotated with respect to one another to further reduce fringe effects and/or cross-talk between the traps.

Additionally, other common mode trap or balun configurations are possible. For example, the exterior shielding of each common mode trap may be trimmed such that the common mode traps can be overlapped or interleaved, thus increasing the density of the common mode traps.

In some examples, the RF coils described above with reference to FIGS. 7-12 may have one of a plurality of different resonant frequencies, and/or one or more RF coils (e.g., of the RF coil arrays described above) may have different resonant frequencies relative to one or more other RF coils. In one example, a gauge of the loop portion of the RF coils, a spacing between wires of the RF coils, a diameter of the loop portion, and/or a number and/or arrangement of cuts in the wires of the RF coils may alter the resonant frequency of the RF coils. RF coils having an appropriate resonant frequency may be selected for various MRI systems (e.g., systems in which the static magnetic field has a specified magnitude, such as 1.5 Tesla, 3 Tesla, 7 Tesla, etc.) and/or may be selected according to an anatomical feature to be imaged by the MRI system (e.g., RF coils for imaging a posterior of the patient may have a different resonant frequency than RF coils for imaging an anterior of the patient).

FIGS. 2-6 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

By configuring the RF coil assembly to include the plurality of flexible sections directly coupled to the flexible spine, the RF coil assembly may be more easily coupled to the body of the patient. The sections may individually bend and/or rotate to enable the RF coil assembly to fit to anatomical features that are difficult to image with conventional, rigid RF coils, such as the brachial plexus. As a result, SNR and patient comfort may be increased. Further, by enabling the RF coil assembly to couple to each side of the body of the patient in a symmetrical fashion, the single RF coil assembly may be utilized to image both of the left and right sides of the patient, and an operating cost of the MRI system may be reduced.

The technical effect of configuring the RF coil assembly to include the plurality of sections is to enable the RF coil assembly to couple to a wider variety patient anatomies.

In one embodiment, a radio frequency (RF) coil assembly for a magnetic resonance imaging (MRI) system comprises: a flexible spine; and at least two RF coil sections each coupled to the flexible spine and movable relative to each other, each RF coil section comprising at least one flexible RF coil, the at least one flexible RF coil including a loop portion comprising a coupling electronics portion and at least two parallel, distributed capacitance wire conductors encapsulated and separated by a dielectric material. In a first example of the RF coil assembly, the RF coil assembly further comprises a coil-interfacing cable extending between each coupling electronics portion and an RF coil interfacing connector, wherein the coil-interfacing cable is coupled to and extends along the flexible spine. A second example of the RF coil assembly optionally includes the first example, and further includes wherein coupling electronics portion includes a pre-amplifier, a decoupling circuit, and an impedance inverter circuit, the impedance inverter circuit comprising an impedance matching network and an input balun, wherein the pre-amplifier comprises a low input impedance pre-amplifier optimized for high source impedance, and wherein the impedance matching network provides the high source impedance. A third example of the RF coil assembly optionally includes one or both of the first and second examples, and further includes wherein the at least two RF coil sections are only coupled to each other via the flexible spine and are not directly coupled to each other at any other location. A fourth example of the RF coil assembly optionally includes one or more or each of the first through third examples, and further includes wherein the at least two RF coil sections comprise four RF coil sections arranged in an overlapping or semi-lapping manner along an axis defined by the flexible spine. A fifth example of the RF coil assembly optionally includes one or more or each of the first through fourth examples, and further includes wherein the four RF coil sections include a first RF coil section configured to cover a neck of a subject to be imaged, a second RF coil section configured to cover a shoulder of the subject, a third RF coil section configured to cover an upper section of an arm of the subject, and a fourth RF coil section configured to cover a lower section of the arm of the subject. A sixth example of the RF coil assembly optionally includes one or more or each of the first through fifth examples, and further includes wherein at least a first RF coil section of the four RF coil sections has a longitudinal axis that is perpendicular to the axis defined by the flexible spine. A seventh example of the RF coil assembly optionally includes one or more or each of the first through sixth examples, and further includes wherein the four RF coil sections include a first RF coil section comprising a first RF coil array including six RF coils arranged in a single row, a second RF coil section comprising a second RF coil array including five RF coils arranged in a single row, a third RF coil section comprising a third RF coil array including five RF coils arranged in a single row, and a fourth RF coil section comprising a fourth RF coil array including ten RF coils arranged in two rows. An eighth example of the RF coil assembly optionally includes one or more or each of the first through seventh examples, and further includes wherein each RF coil of the first RF coil array has a first diameter and each RF coil of the second RF coil array has a second diameter, the second diameter larger than the first diameter. A ninth example of the RF coil assembly optionally includes one or more or each of the first through eighth examples, and further includes wherein at least one RF coil section is coupled to two respective straps.

In another embodiment, a radio frequency (RF) coil assembly for a magnetic resonance imaging (MRI) system comprising: a flexible spine; a first RF coil array section coupled to the flexible spine only along a top edge of the first RF coil array section and including a first RF coil array comprising a plurality of flexible RF coils; a second RF coil array section coupled to the flexible spine only along a top edge of the second RF coil array section and including a second RF coil array comprising a plurality of flexible RF coils, each of the first RF coil array section and the second RF coil array section having at least 90 degrees of rotation along a respective interface with the flexible spine, and each RF coil including a loop portion comprising a coupling electronics portion and at least two parallel, distributed capacitance wire conductors encapsulated and separated by a dielectric material. In a first example of the RF coil assembly, the RF coil assembly further comprises: a third RF coil array section coupled to the flexible spine only along a top edge of the third RF coil array section and including a third RF coil array comprising a plurality of flexible RF coils; and a fourth RF coil array section coupled to the flexible spine only along a top edge of the fourth RF coil array section and including a fourth RF coil array comprising a plurality of flexible RF coils, each of the third RF coil array section and the fourth RF coil array section having at least 90 degrees of rotation along a respective interface with the flexible spine. A second example of the RF coil assembly optionally includes the first example, and further includes wherein a bottom edge of the second RF coil array section overlaps the top edge of the third RF coil array section and a bottom edge of the third RF coil array section overlaps with the top edge of the fourth RF coil array section. A third example of the RF coil assembly optionally includes one or both of the first and second examples, and further includes wherein the first RF coil array section has a longitudinal axis and the flexible spine has a central axis, the longitudinal axis perpendicular to the central axis. A fourth example of the RF coil assembly optionally includes one or more or each of the first through third examples, and further includes wherein the first RF coil array section has a length that extends along the longitudinal axis and the flexible spine has a width that extends perpendicular to the central axis and parallel to the length, wherein the width is less than half of the length.

In another embodiment, a radio frequency (RF) coil assembly for a magnetic resonance imaging (MRI) system comprises: a flexible spine; four RF coil array sections each coupled to the flexible spine and movable relative to each other, including a first RF coil array section configured to cover a neck of a subject to be imaged, a second RF coil array section configured to cover a shoulder of the subject, a third RF coil array section configured to cover an upper section of an arm of the subject, and a fourth RF coil array section configured to cover a lower section of the arm of the subject, each RF coil array section comprising a respective RF coil array including a plurality of flexible RF coils, each RF coil including a loop portion comprising a coupling electronics portion and at least two parallel, distributed capacitance wire conductors encapsulated and separated by a dielectric material; and a coil-interfacing cable extending between each coupling electronics portion and an RF coil interfacing connector, wherein the coil-interfacing cable is coupled to and extends along the flexible spine. In a first example of the RF coil assembly, the first RF coil array section includes a first RF coil array including six RF coils arranged in a single row, the second RF coil array section includes a second RF coil array including five RF coils arranged in a single row, the third RF coil array section includes a third RF coil array including five RF coils arranged in a single row, and the fourth RF coil array section includes a fourth RF coil array including ten RF coils arranged in two rows. A second example of the RF coil assembly optionally includes the first example, and further includes wherein the four RF coil array sections are only coupled to each other via the flexible spine and are not directly coupled to each other at any other location. A third example of the RF coil assembly optionally includes one or both of the first and second examples, and further includes wherein each of the four RF coil array sections are configured to move in an upward direction, away from the flexible spine, around respective rotational axes defined by respective interfaces between each RF coil array section and the flexible spine. A fourth example of the RF coil assembly optionally includes one or more or each of the first through third examples, and further includes wherein each of the first RF coil array section, second RF coil array section, third RF coil array section, and fourth RF coil array section is centered along a central axis of the flexible spine.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A radio frequency (RF) coil assembly for a magnetic resonance imaging (MRI) system, comprising:
   a flexible spine;
   at least two RF coil sections only coupled to each other via the flexible spine and not directly coupled to each other at any other location and movable relative to each other, each RF coil section comprising at least one flexible RF coil, each RF coil including a loop portion comprising a coupling electronics portion and at least two parallel, distributed capacitance wire conductors encapsulated and separated by a dielectric material, wherein each of the distributed capacitance wire conductors includes a first terminating end and a second terminating end;
   wherein the coupling electronics portion includes a pre-amplifier, a decoupling circuit, and an impedance inverter circuit;
   wherein the decoupling circuit includes a decoupling diode which when turned on causes the at least two parallel wire conductors to short, wherein the decoupling diode is directly connected between at least two first terminating ends of the at least two distributed capacitance wire conductors;
   wherein the impedance inverter circuit comprises an impedance matching network and an input balun having two input terminals and two output terminals, wherein the pre-amplifier comprises a low input impedance pre-amplifier optimized for high source impedance, and wherein the impedance matching network provides the high source impedance;
   wherein the input balun is connected between the decoupling diode and the impedance matching network and wherein the second terminating end of one of the at least two distributed capacitance wire conductors is directly connected to one input end of the input balun; and
   wherein the flexible spine section is devoid of RF coils.

2. The RF coil assembly of claim 1, further comprising a coil-interfacing cable extending between each coupling electronics portion and an RF coil interfacing connector, wherein the coil-interfacing cable is coupled to and extends along the flexible spine.

3. The RF coil assembly of claim 1, wherein the at least two RF coil sections comprise four RF coil sections arranged in an overlapping or semi-lapping manner along an axis defined by the flexible spine.

4. The RF coil assembly of claim 3, wherein the four RF coil sections include a first RF coil section configured to cover a neck of a subject to be imaged, a second RF coil section configured to cover a shoulder of the subject, a third RF coil section configured to cover an upper section of an arm of the subject, and a fourth RF coil section configured to cover a lower section of the arm of the subject.

5. The RF coil assembly of claim 3, wherein at least a first RF coil section of the four RF coil sections has a longitudinal axis that is perpendicular to the axis defined by the flexible spine.

6. The RF coil assembly of claim 3, wherein the four RF coil sections include a first RF coil section comprising a first RF coil array including six RF coils arranged in a single row, a second RF coil section comprising a second RF coil array including five RF coils arranged in a single row, a third RF coil section comprising a third RF coil array including five RF coils arranged in a single row, and a fourth RF coil section comprising a fourth RF coil array including ten RF coils arranged in two rows.

7. The RF coil assembly of claim 6, wherein each RF coil of the first RF coil array has a first diameter and each RF coil of the second RF coil array has a second diameter, the second diameter larger than the first diameter.

8. The RF coil assembly of claim 3, wherein at least one RF coil section is coupled to two respective straps.

9. The RF coil assembly of claim 1, wherein a length of the distributed capacitance wire conductors is varied to achieve a desired value of the distributed capacitance.

10. The RF coil assembly of claim 1, wherein the at least two distributed capacitance wire conductors include planar strips.

11. The RF coil assembly of claim 1, wherein the coupling electronics portion includes a pre-amplifier having an impedance value which is less than 5 ohms at a resonance frequency.

12. The RF coil assembly of claim 1, wherein the at least two distributed capacitance wire conductors are continuous along an entire length of the loop portion.

13. The RF coil assembly of claim 1, wherein the low input impedance pre-amplifier is optimized for high source impedance of at least 500 ohms.

14. The RF coil assembly of claim 1, wherein the one of the two output terminals of the input balun is connected to a ground connection and the other output terminal is connected to the impedance matching network.

15. The RF coil assembly of claim 1, wherein the loop portion includes at least one cut or gap in in at least one of the two parallel, distributed capacitance wire conductors.

16. The RF coil assembly of claim 1, wherein the direct coupling between the at least two RF coil sections and the flexible spine does not include positioning the two RF coil sections in contact with each other without fastening or fusing.

17. A radio frequency (RF) coil assembly for a magnetic resonance imaging (MRI) system, comprising:
  a flexible spine;
  a first RF coil array section coupled to the flexible spine only along a top edge of the first RF coil array section and including a first RF coil array comprising a plurality of flexible RF coils;
  a second RF coil array section coupled to the flexible spine only along a top edge of the second RF coil array section and including a second RF coil array comprising a plurality of flexible RF coils, each of the first RF coil array section and the second RF coil array section being formed of a flexible material and having at least 90 degrees of rotation along a respective interface with the flexible spine, and
  each RF coil including a loop portion comprising a coupling electronics portion and at least two parallel, distributed capacitance wire conductors encapsulated and separated by a dielectric material, wherein each of the distributed capacitance wire conductors includes a first terminating end and a second terminating end;
  wherein the coupling electronics portion includes a pre-amplifier, a decoupling circuit, and an impedance inverter circuit;
  wherein the decoupling circuit includes a decoupling diode which when turned on causes the at least two parallel wire conductors to short, wherein the decoupling diode is directly connected between at least two first terminating ends of the at least two distributed capacitance wire conductors;
  wherein the impedance inverter circuit comprises an impedance matching network and an input balun having two input terminals and two output terminals, wherein the pre-amplifier comprises a low input impedance pre-amplifier optimized for high source impedance, and wherein the impedance matching network provides the high source impedance;
  wherein the input balun is connected between the decoupling diode and the impedance matching network and wherein the second terminating end of one of the at least two distributed capacitance wire conductors is directly connected to one input end of the input balun; and
  wherein the flexible spine section is devoid of RF coils.

18. The RF coil assembly of claim 17, further comprising:
  a third RF coil array section coupled to the flexible spine only along a top edge of the third RF coil array section and including a third RF coil array comprising a plurality of flexible RF coils; and
  a fourth RF coil array section coupled to the flexible spine only along a top edge of the fourth RF coil array section and including a fourth RF coil array comprising a plurality of flexible RF coils, each of the third RF coil array section and the fourth RF coil array section having at least 90 degrees of rotation along a respective interface with the flexible spine.

19. The RF coil assembly of claim 18, wherein a bottom edge of the second RF coil array section overlaps the top edge of the third RF coil array section and a bottom edge of the third RF coil array section overlaps with the top edge of the fourth RF coil array section.

20. The RF coil assembly of claim 17, wherein the first RF coil array section has a longitudinal axis and the flexible spine has a central axis, the longitudinal axis perpendicular to the central axis.

21. The RF coil assembly of claim 20, wherein the first RF coil array section has a length that extends along the longitudinal axis and the flexible spine has a width that extends perpendicular to the central axis and parallel to the length, wherein the width is less than half of the length.

22. A radio frequency (RF) coil assembly for a magnetic resonance imaging (MRI) system, comprising:
  a flexible spine;
  four RF coil array sections being formed of a flexible material only coupled to each other via the flexible spine and not directly coupled to each other at any other location and movable relative to each other, including a first RF coil array section configured to cover a neck of a subject to be imaged, a second RF coil array section configured to cover a shoulder of the subject, a third RF coil array section configured to cover an upper section of an arm of the subject, and a fourth RF coil array section configured to cover a lower section of the arm of the subject,
  each RF coil array section comprising a respective RF coil array including a plurality of flexible RF coils, each RF coil including a loop portion comprising a coupling electronics portion and at least two parallel, distributed capacitance wire conductors encapsulated and separated by a dielectric material, wherein each of the distributed capacitance wire conductors includes a first terminating end and a second terminating end;
  a coil-interfacing cable extending between each coupling electronics portion and an RF coil interfacing connector, wherein the coil-interfacing cable is coupled to and extends along the flexible spine;
  wherein the coupling electronics portion includes a pre-amplifier, a decoupling circuit, and an impedance inverter circuit; and
  wherein the decoupling circuit includes a decoupling diode which when turned on causes the at least two parallel wire conductors to short, wherein the decoupling diode is directly connected between at least two first terminating ends of the at least two distributed capacitance wire conductors;
  wherein the impedance inverter circuit comprising an impedance matching network and an input balun having two input terminals and two output terminals, wherein the pre-amplifier comprises a low input impedance pre-amplifier optimized for high source impedance, and wherein the impedance matching network provides the high source impedance;
  wherein the input balun is connected between the decoupling circuit diode and the impedance matching network and wherein the second terminating end of one of the at least two distributed capacitance wire conductors is directly connected to one input end of the input balun; and
  wherein the flexible spine section is devoid of RF coils.

23. The RF coil assembly of claim 22, wherein the first RF coil array section includes a first RF coil array including six RF coils arranged in a single row, the second RF coil array section includes a second RF coil array including five RF coils arranged in a single row, the third RF coil array section includes a third RF coil array including five RF coils arranged in a single row, and the fourth RF coil array section includes a fourth RF coil array including ten RF coils arranged in two rows.

24. The RF coil assembly of claim 22, wherein each of the first RF coil array section, second RF coil array section, third RF coil array section, and fourth RF coil array section is centered along a central axis of the flexible spine.

25. The RF coil assembly of claim 22, wherein each of the first RF coil array section, second RF coil array section, third RF coil array section, and fourth RF coil array section is formed of a flexible material that is transparent to RF signals.

26. The RF coil assembly of claim 25, wherein the flexible RF coils are configured to bend along with the flexible material without degradation of signals associated with the RF coils.

* * * * *